(12) United States Patent
Sackstein

(10) Patent No.: US 8,633,026 B2
(45) Date of Patent: Jan. 21, 2014

(54) CYTOKINE INDUCTION OF SELECTIN LIGANDS ON CELLS

(75) Inventor: Robert Sackstein, Sudbury, MA (US)

(73) Assignee: Robert Sackstein, Sudbury, MA (US)

( * ) Notice: Subject to any disclaimer, the term of this patent is extended or adjusted under 35 U.S.C. 154(b) by 167 days.

(21) Appl. No.: 13/038,977

(22) Filed: Mar. 2, 2011

(65) Prior Publication Data

US 2011/0177040 A1 Jul. 21, 2011

Related U.S. Application Data

(62) Division of application No. 11/779,650, filed on Jul. 18, 2007, now Pat. No. 7,998,740.

(60) Provisional application No. 60/831,525, filed on Jul. 18, 2006.

(51) Int. Cl.
*C12N 5/078* (2010.01)
*C12N 5/0786* (2010.01)
*C12N 5/0787* (2010.01)
*A61K 31/35* (2006.01)

(52) U.S. Cl.
USPC ............ 435/377; 514/7.9; 514/451; 424/93.1

(58) Field of Classification Search
None
See application file for complete search history.

(56) References Cited

PUBLICATIONS

Katayama et al., J Exp Med. Apr. 18, 2005; 201(8): 1183-1189.*
Katoh et al., The Journal of Immunology, 1999, 162: 5058-5061.*

* cited by examiner

*Primary Examiner* — Daniel C Gamett
(74) *Attorney, Agent, or Firm* — Bryan Cave LLP

(57) ABSTRACT

Methods and compositions for treating cells with cytokines are provided herein.

20 Claims, 19 Drawing Sheets

SEQUENCE LISTING

```
<160> NUMBER OF SEQ ID NOS: 8

<210> SEQ ID NO 1
<211> LENGTH: 46
<212> TYPE: DNA
<213> ORGANISM: Artificial Sequence
<220> FEATURE:
<223> OTHER INFORMATION: Chemically Synthesized

<400> SEQUENCE: 1
ctctccgata tctgttttat tttcccatcc cagagagaag aaggag                46

<210> SEQ ID NO 2
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 2
gattaaggta ccaggtcaga aggaggtgag gttctt                           36

<210> SEQ ID NO 3
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 3
cccaccgtgg cccagtacta ccgcttct                                   28

<210> SEQ ID NO 4
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 4
ctgacctctg tgcccagcct cccgt                                      25

<210> SEQ ID NO 5
<211> LENGTH: 24
<212> TYPE: DNA
<213> ORGANISM: Artificial Sequence
<220> FEATURE:
```

```
<223> OTHER INFORMATION: Chemically Synthesized

<400> SEQUENCE: 5
cgggtgtgcc aggctgtaca gagg                                              24

<210> SEQ ID NO 6
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 6
tcgggaacag ttgtgtatga gatt                                              24

<210> SEQ ID NO 7
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 7
gaaggtgaag gtcggagtc                                                    19

<210> SEQ ID NO 8
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 8
aagatggtga tgggatttc                                                    19
```

CYTOKINE INDUCTION OF SELECTIN LIGANDS ON CELLS

RELATED APPLICATIONS

This application is a Divisional of U.S. patent application Ser. No. 11/779,650, filed Jul. 18, 2007, which claims priority to U.S. Provisional Application No. 60/831,525, filed Jul. 18, 2006, which is incorporated herein by reference in its entirety.

STATEMENT AS TO FEDERALLY SPONSORED RESEARCH

The work described herein was funded, in part through a grant from the National Institutes of Health (grant RO1 HL060528). The United States government has certain rights in the invention.

FIELD OF THE INVENTION

This invention relates to methods and compositions for modulating cell expression of glycoproteins and glycolipids. The invention also describes reagents and methods of modulating E-selectin ligand activity, e.g., in cases where cytokine-induced E-selectin ligand expression are associated with adverse effects.

BACKGROUND

The capacity to direct migration of blood-borne cells to a predetermined location ("homing") has profound implications for a variety of physiologic and pathologic processes. Recruitment of circulating cells to a specific anatomic site is initiated by discrete adhesive interactions between cells in flow and vascular endothelium at the target tissue(s).

Selectin-mediated interactions are critical not only for the rapid and efficient recruitment of leukocytes at a site of injury, but for steady state, tissue-specific homing as illustrated in: (1) lymphocyte homing to peripheral lymph nodes, (2) cutaneous tropism of human skin-homing T-cells and (3) hematopoietic progenitor cell (HPC) entry into bone marrow.

SUMMARY

The invention is based, in part, on the discovery of methods and compositions for modulating the expression or activity of glycosylation enzymes in a cell. The methods increase the expression or activity of a glycosylated cell-surface molecule, such as a glycolipid or glycoprotein (e.g., a glycolipid or glycoprotein that binds a selectin). The glycosylation enzyme is a glycosyltransferase such as α2,3-sialyltransferase (ST3GalIV), leukocyte α1,3-fucosyltransferases (FucT-IV, FucT-VII or FucT-IX), or glycosyltransferase core 2 β1-6 N-acetylglucosaminyl transferase (C2GnT1 or C2GlcNAcT1) or a glycosidase such sialidase. The methods and compositions described herein are particularly useful for augmenting selectin ligand or lewis antigen (e.g. CDS15) expression or activity on various cell types, and can be applied to enhance the engraftment and/or tissue-regenerative potential of cells. Accordingly, in one aspect, the invention features a method for treating a cell by contacting the cell with one or more cytokines that increase the expression or activity of a glycosyltransferase polypeptide or glycosidase polypeptide in a cell. For example the cell is contacted with two, three, four, five or more cytokines. The method increases cell-surface expression or activity of a selectin ligand, a lewis antigen (e.g., lewis x), a VIM-2 epitope or a HECA-452-reactive epitope on the cell. A selectin ligand is a glycoprotein or a glycolipid. For example the selectin ligand is an E-selectin ligand, an L-selectin ligand, a P-selectin ligand. In various embodiments, the cytokine increases the cell-surface expression or activity of an E-selectin ligand on the cell. The E-selectin ligand is, for example, Hematopoietic Cell E-/L-selectin Ligand (HCELL), or the ~65 kDa E-selectin described herein. In various embodiments, the method increases the affinity of the cell for a selectin.

The cell can be a hematopoietic cell, such as a hematopoietic stem cell, e.g., a CD34+ hematopoietic stem cell, a peripheral blood leukocyte, a lymphocyte, or a myeloid cell, such as an immature myeloid cell. Other types of cells, including non-hematopoietic cells, may also be treated according to the methods. Appropriate non-hematopoietic cells express a receptor for the cytokine of interest. For example, glial and neuronal cells express receptors for granulocyte colony stimulating factor (G-CSF). Neurons are also sensitive to macrophage colony-stimulating factor (M-CSF) and interleukin-3 (IL-3).

In various embodiments, the cytokine modulates selectin ligand expression selectively, on a particular type of cell (e.g., the cytokine selectively acts on hematopoietic cells or another subset of cells). In various embodiments, the cell contacted with the cytokine is not a T cell.

In various embodiments, a plurality of cells is provided. A cell can be provided ex vivo, or in vivo. The cell can also be contacted with the cytokine in vitro.

The cytokine is contacted with the cell in a concentration range of 1-1,000 ng/ml, 1-100 ng/ml, 1-50 ng/ml, 1-25 ng/ml, or 1-10 ng/ml.

Suitable cytokines include those that modulate the expression or activity of a selectin ligand and/or enzymes that modulate the selectin-binding activity of a selectin ligand, such as carbohydrate modifying enzymes such that expression of selectin-binding epitopes increases. In one embodiment, the cytokine is granulocyte colony stimulating factor (G-CSF). Alternatively, the cytokine is granulocyte macrophage colony stimulating factor (GM-CSF), macrophage colony stimulating factor (M-CSF), interleukin-3 (IL-3)/multi colony stimulating factor (Multi-CSF), transforming growth factor β (TGFβ), an interferon, a chemokine, an interleukin or a tumor necrosis factor. An interleukin includes, for example, IL-1, IL-2, IL-4, IL-5, IL-6, IL-7, IL-8, IL-9, IL-10, IL-11, IL-13, IL-14, IL-15, IL-16, IL-17, IL-18, IL-19, IL-20, IL-21, IL-22, IL-23, IL-24, IL-25, IL-26, IL-27, IL-28, and IL-29.

The cell is treated ex vivo, and the method further includes administering the cell, or a plurality of cells, to a subject, e.g., a subject in need of treatment for tissue injury, and/or cell as part of a hematopoietic stem cell transplantation protocol. Optionally, the cells which are administered are a selected subset of cells (e.g., a subset which have been selected based on a particular phenotype or expression of a cell surface marker, such as a stem cell marker). The cells may be enriched for those which express high levels of the selectin ligand. Additionally, the method includes selecting a subpopulation of cells (e.g., a subpopulation of leukocytes, or stem cells, such as hematopoietic stem cells, or stem cells which support regeneration of a desired tissue) prior to contacting the cells with a cytokine.

In another aspect, the invention features a kit for treatment of a cell to increase its engraftment and/or regenerative potential. The kit includes, for example: a composition comprising a cytokine (e.g., G-CSF), and instructions for use of the cytokine to treat a cell under conditions in which the cytokine increases the cell-surface expression or activity of a selectin ligand polypeptide on the cell, thereby increasing the engraftment and/or regenerative potential of the cell.

In another aspect, the invention features a composition comprising a glycoprotein isolated from granulocyte colony stimulating factor-treated peripheral blood leukocytes, wherein the glycoprotein is approximately 65 kDa, is reactive with monoclonal antibody HECA-452, and is a ligand for E-selectin. The glycoprotein may be purified or isolated. In various embodiments, the glycoprotein includes other features described herein. The invention also includes derivatives of the 65 kDa glycoprotein which compete with the natural 65 kDa glycoprotein for binding to E-selectin.

In another aspect, the invention features a method for treating a subject who has received, or is scheduled to receive granulocyte colony stimulating factor (G-CSF). The method include: administering to the subject an agent which inhibits a selectin-mediated (e.g., E-selectin-mediated) interaction with a selectin ligand. In various embodiments, the method reduces side effects due to administration of G-CSF, such as enhanced leukocyte-endothelial interactions that are associated with adverse inflammatory reactions. The agent is, for example, an antibody or antigen-binding fragment thereof, a small interfering RNA, or an antisense oligonucleotide. In various embodiments, the agent inhibits the expression or activity of a glycosyltransferase and/or interferes with carbohydrate synthesis. The agent may also be a soluble carbohydrate or glycosylated polypeptide which directly inhibits an interaction between a selectin and a selectin ligand, e.g., by competition for binding to either the selectin or the selectin ligand. Examples of suitable agents include soluble mimetics of selectin ligands. The agent can be a soluble form of a natural selectin, selectin ligand or a derivative thereof which exhibits enhanced affinity for the selectin ligand or for the selectin, respectively, or to both.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

shows rolling velocity of untreated or G-CSF-treated cells on stimulated HUVEC. Stim. indicates pretreatment (+) or no pretreatment (−) of HUVEC with IL-1β for 4-6 hours prior to the assay; α-E-sel indicates pretreatment (+) or no pretreatment (−) of HUVEC with a function blocking mAb to E-selectin, (68-5411); EDTA indicates presence (+) or absence (−) of 5 mM EDTA in the assay buffer. Values are means±SE of n≥5 different runs. * indicates statistically significant difference (p<0.05).

Figure 13:
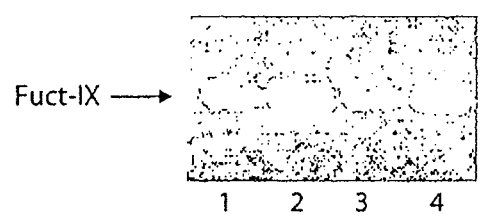

FIG. 13 illustrates that G-CSF treatment increases Fuct-IX expression in normal progenitors and in mobilized peripheral blood. Lane 1 are normal cells isolated from bone marrow from healthy donor. Lane 2 are G-CSF treated normal progenitors isolated from bone marrow from healthy donor. Lane 3 are untreated cells isolated from G-CSF mobilized blood. Lane 4 are G-CSF treated cells isolated from G-CSF mobilized blood.

Figure 14:
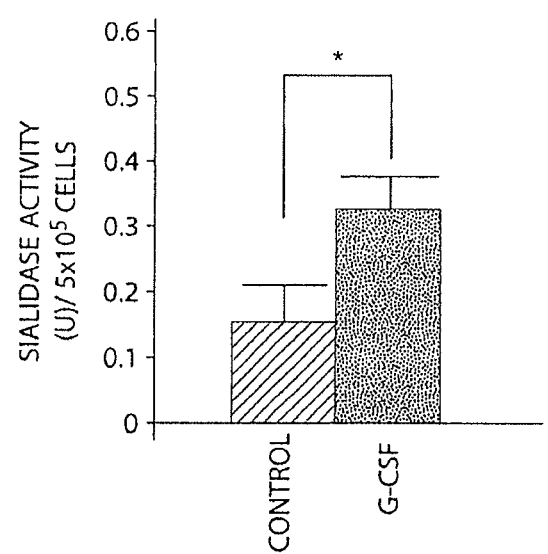

FIG. 14 is a bar graph showing that G-CSF treatment of human myeloid bone marrow cells increases sialidase activity. Sialidase activity from human myeloid cells (obtained from bone marrow of normal subjects), before and after treatment with 10 ng/mL of G-CSF for 24 hours was measured using 4-MU-NANA as subtrate, * indicates significantly different (p<0.05).

Figure 15:
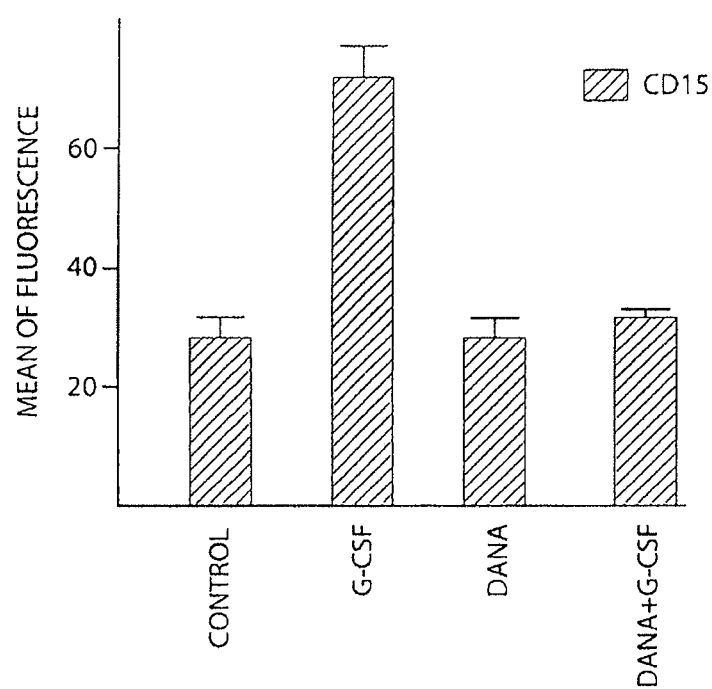

FIG. 15 is a bar graph illustrating that inhibition of sialidase with DANA blunts G-CSF-induced increase in CD15. Bone marrow cells were treated with 10 ng/mL of G-CSF for 5 days in the presence or absence of 100 mM DANA and expression of CD15 was analyzed by flow cytometry.

Like reference symbols in the various drawings indicate like elements.

DETAILED DESCRIPTION

The invention is based in part on the surprising discovery that cytokines can induce the expression of glycosylation enzymes in a cell. Specifically, G-CSF induced the expression of glycosyltranferases in a cell which resulted in the increased expression of hematopoietic cell E-/L-selectin ligand (HCELL) and an approximately 65 kDa E-selectin ligand. Additionally, G-CSF induced the expression of sialidase which resulted in an increased expression of CD15.

Granulocyte colony stimulating factor (G-CSF) is widely used clinically to augment neutrophil recovery after myelo-suppressive chemo/radiotherapy and for mobilizing bone marrow (BM) hematopoietic progenitors for use in hematopoietic stem cell transplantation (HSCT)[1]. Though generally considered safe, there are increasing observations that G-CSF administration can promote leukocyte-endothelial adhesive interactions resulting in vascular and inflammatory complications[2-13]. Indeed, G-CSF administration has been shown to (i) recruit neutrophils to lung vasculature resulting in respiratory distress syndrome[4-6], (ii) stimulate granulocyte adherence to endothelium resulting in angina pectoris/myocardial infarct[7], (iii) cause neutrophil infiltration in dermal vessels[8,9] leading to development of cutaneous leukocytoclastic vasculitis[10], (iv) intensify arthritic symptoms[11] and (v) precipitate sickle cell vaso-occlusion[12]. Though G-CSF administration may have favorable effects on myocardial recovery following infarct in preclinical models[14], a recent report of G-CSF administration in patients with coronary artery disease revealed a striking incidence of cardiac ischemic complications[13]. A better understanding of the molecular basis of the enhanced leukocyte-endothelial interactions accompanying clinical G-CSF administration could yield strategies to prevent these complications.

Despite decades of clinical observations on G-CSF biology, the effects of G-CSF administration on leukocyte membrane molecules that bind endothelial counter-receptors under hemodynamic shear conditions are unknown. In this study, the capacity of leukocytes mobilized by G-CSF (ML) to bind to inflamed (TNF-α-stimulated) endothelium was evaluated. Parallel plate assays conducted under physiologic flow conditions and intravital microscopy of a murine inflammation model each showed that, compared to NL, ML display markedly increased adhesive interactions with inflamed endothelium, mediated by enhanced E-selectin receptor/ligand interactions. ML expressed the potent E-selectin ligand HCELL and another heretofore unrecognized E-selectin glycoprotein ligand of ~65 kDa, and possessed enhanced levels of critical glycosyltransferases (ST3GalIV, FucT-IV, FucT-VII and FucT-IX) rendering E-selectin ligand activity. Enzymatic removal of PSGL-1 revealed that these novel ligands are the principal mediators of the robust ML adhesion to vascular E-selectin. Treatment of normal human BM cells with clinically-relevant serum levels of G-CSF in vitro increased the expression of pertinent glycosyltransferases directly inducing the expression of these two ligands and resulting in enhanced E-selectin-mediated endothelial binding. Collectively, these results provide first evidence that enhanced leukocyte-endothelial interactions following G-CSF administration is mediated by G-CSF-induced expression of counter-receptors for vascular E-selectin among circulating myeloid cells and offer mechanistic insights on the molecular basis of G-CSF-induced increased E-selectin ligand activity.

Figure 3E:
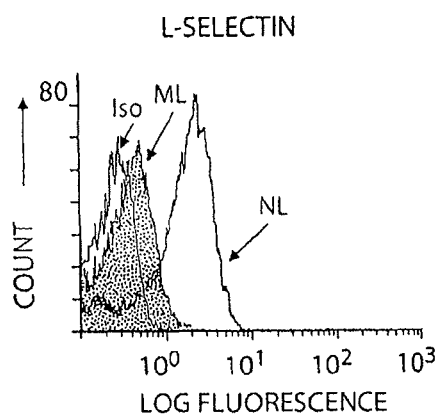
Figure 4A:
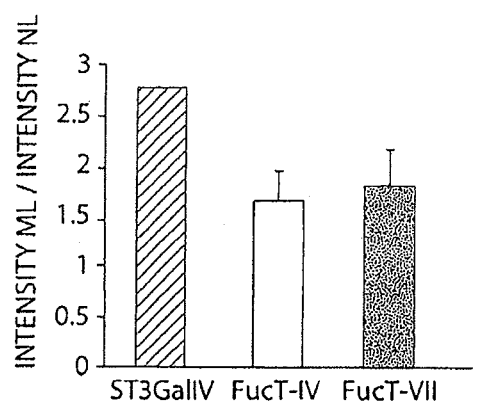
FIGS. 4A-B illustrates ML possess enhanced levels of glycosyltransferases ST3GalIV, FucT-IV and FucT-VII. Total RNA from equal numbers of ML and NL was subjected to RT-PCR followed by PCR amplification of pairs of cDNAs for ST3GalIV, FucT-IV, FucT-VII and the housekeeping gene GAPDH. (A) Shows the net intensity of amplified bands was normalized to the net intensity of respective GAPDH controls. All values are means±SE of at least 3 different experiments. (B) Shows that typical blots of PCR amplified products from NL and ML RNA are presented.
Figure 4B:
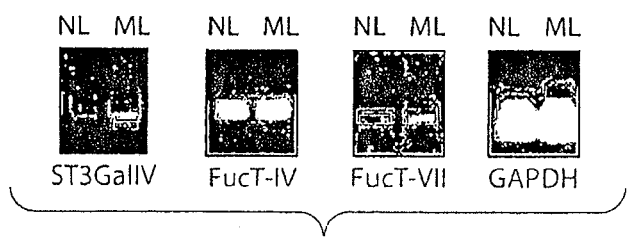

In this study, no distinct change in HECA-452 reactivity of PSGL-1 on ML compared to that of NL (FIG. 2a) was observed. Furthermore, OSGE treatment of ML decreased PSGL-1 expression and function without affecting the overall E-selectin binding capacity of ML (FIG. 4). Interestingly, ML possessed diminished P-selectin binding compared to NL (FIG. 11) suggesting that PSGL-1 function is also altered on ML. Consistent with prior studies[34], we observed marked decrease in surface L-selectin expression on circulating leukocytes following G-CSF administration (FIG. 3e), excluding a role for L-selectin as an E-selectin ligand on ML.

In contrast to the broad distribution of PSGL-1, HCELL is characteristically found primarily on normal human BM CD34+ progenitors[28,39]. Herein, biochemical studies of ML show that G-CSF administration results in robust HCELL expression on circulating (mobilized) myeloid cells, most prominently on immature myeloid cells (FIG. 6b). The observed augmented HCELL expression is a direct effect of G-CSF, as exposure to pharmacologically-relevant G-CSF concentrations in vitro[44,45] results in increases in glycosyl-transferases and the elaboration of HECA-452-reactive glycosylations rendering the HCELL phenotype on immature human BM myeloid cells (FIG. 6c). Though low level expression of HCELL on native circulating human PMNs is observed occasionally, G-CSF had only a variable effect on inducing HCELL expression among mature myeloid BM cells. Importantly, HCELL is not expressed on lymphocytes in BM or in blood, and it is not induced on lymphocytes by G-CSF treatment.

In addition to induction of HCELL, G-CSF administration in vivo and in vitro also induces the expression of a HECA-452-reactive ~65 kDa glycoprotein. The results of blot-rolling assays, Western blot staining with E-Ig, and immunoprecipitation with E-Ig of membrane preparations of ML show that the ~65 kDa glycoprotein is a high affinity E-selectin ligand. The G-CSF-induced ~65 kDa E-selectin ligand does not appear to be a glycoform of other previously described E-selectin ligands (PSGL-1, CD44, and L-selectin (FIG. 3)), and thus represents a novel E-selectin ligand. Importantly, this ~65 kDa glycoprotein is found predominantly among cells within the mononuclear fraction of ML (ML-M cells) (FIG. 6b). Although the various leukocyte subset(s) that express this ~65 kDa glycoprotein are currently unknown and warrant further investigation, its expression is conspicuously absent from lymphocytes (both T- and B-cells) within the ML-M fraction.

From a clinical perspective, defining the molecular mechanism(s) of G-CSF-induced vascular and inflammatory complications is of paramount importance as healthy individuals are increasingly being exposed to this agent to serve as donors for hematopoietic stem cell therapy (HSCT). It is plausible that G-CSF may preferentially mobilize subset(s) of myeloid cells which express high affinity E-selectin ligands. Consistent with this notion are clinical observations that G-CSF-associated adverse events occur in parallel to increases in leukocyte numbers[4,9,12]. However, not all donors with high leukocyte counts will exhibit complications, suggesting that some individuals may be particularly susceptible to G-CSF-induced vascular and inflammatory problems. To some extent, this may reflect variabilities in the capacity of G-CSF to induce E-selectin ligand expression on circulating myeloid cells and/or responsiveness of the endothelial cells of G-CSF recipients to the induction of E-selectin expression. However, in multiple clinical ML collections, it was observed that G-CSF uniformly increased E-selectin ligand activity of circulating leukocytes and upregulated the expression of the E-selectin ligands HCELL and the HECA-452-reactive ~65 kDa glycoprotein. The cumulative effect of these additional, G-CSF-induced E-selectin ligands to that of natively expressed PSGL-1 on immature (and mature) myeloid cells may prime these circulating cells to adhere to inflamed/ischemic endothelium, consistent with emerging clinical experiences/reports raising warnings for the use of G-CSF in individuals with known or suspected inflammatory or cardiovascular diseases.

Under physiologic blood flow conditions, leukocytes initially make contact on the vessel surface by engagement of counter-receptors for relevant endothelial molecules that mediate shear-resistant interactions[15,16]. One of the principal effectors of these interactions is E-selectin, which is an inducible endothelial molecule expressed at sites of inflammation[16,17] that binds sialofucosylated carbohydrate ligands expressed on leukocytes[18]. An expanding body of evidence causally links upregulated E-selectin expression to vascular complications of G-CSF administration[19-22]. Notably, the receptor for G-CSF is expressed on endothelium[23] and G-CSF directly induces E-selectin expression on endothelial cells in culture[24]. However, there is little information on whether G-CSF administration modifies E-selectin ligand expression on mobilized, circulating leukocytes.

These findings provide new perspectives on selectin ligands and on the biology of G-CSF, and indicate that induction of potent counter-receptors for E-selectin is contributory to the vascular and inflammatory complications observed with the use of this agent.

Methods of Increasing Glycosylation Enzyme Expression or Activity

Glycosylation enzyme expression or activity in a cell is increased by contacting a cell with a cytokine. Glycosylation enzymes include for example glycosytransferases or glycosidases. Glycosyltransferase catalyze the transfer of glycosyl groups to an acceptor and are responsible for the formation of glycosidic bonds. In contrast, glycosidases catalyze hydrolysis of the glycosidic linkage and are responsible for the trimming of glycans during carbohydrate synthesis. Glycosyltransferases and glycosidases form the major catalytic machinery for the synthesis and breakage of glycosidic bonds involved in carbohydrate synthesis.

Glycosyltransferase includes for example, core 1 glycosyltransferase (e.g., β-3-galactosyltransferase); core 2 glycosyltransferase (e.g., N-acetylglucosaminyltransferases such as β-(1,6) N-acetylglucosaminyltransferase, GnTI, GnTII, GnTIII, GlcNAcT1; sialyltransferases (e.g., α-sialyltransferases, such as α-2,3 sialyltransferases (ST3GalIV) α-2,6 sialyltransferases, and β-sialyltransferases); fucosyltransferases (e.g., α-fucosyltransferases, such as α-1,3 fucosyltransferases (FucT IV, FucT VII, FucT IX) and β-fucosyltransferases; galactosyltransferases; (e.g., α-galactosyltransferases, such as α1,3 galactosyltransferases and β-galactosyltransferases); mannosyltransferases (e.g., α-mannosyltransferases and β-mannosyltransferases), or N-acetylgalactosaminyltransferases (e.g., α-(1,3) N-acetylgalactosaminyltransferase and β-(1,4) N-acetylgalactosaminyltransferases).

Glycosidases include for example glucosidases, mannosidases, fucosidases, sialidases, galactosidases, xylanases, lactases, amylases, chitinases, sucrases, maltases, neuraminidases, invertases, hyaluronidase or lysozymes.

Cytokines include for example, granulocyte colony stimulating factor (G-CSF), granulocyte macrophage colony stimulating factor (GM-CSF), macrophage colony stimulating factor (M-CSF), interleukin-3 (IL-3)/multi colony stimulating factor (Multi-CSF), transforming growth factor β(TGFβ), an interferon, a chemokine, a tumor necrosis factor or an interleukin, such as interleukin-1 (IL-1) IL-2, IL-3, IL-4, IL-5, IL-6, IL-7, IL-8, IL-9, IL-10, IL-11, IL-12, IL-13, IL-15, IL-14, IL-16, IL-17, IL-18, IL-19, IL-20, IL-21, IL-22, IL-23, IL-24, IL-25, IL-26, IL-27, IL-28, and IL-29.

Cells to be treated include any cell capable of expressing a glycoprotein or a glycolipid. The cell is a hematopoietic cell, such as a hematopoietic stem cell, e.g., a CD34+ hematopoietic stem cell, a bone marrow cell, a neutrophil, a peripheral blood leukocyte, a lymphocyte, or a myeloid cell, such as an immature myeloid cell. Alternatively, the cell is a non-hematopoietic cells such as a liver cell, a lung cell, a pancreatic cell, a cardiac cell, a gastric cell or a kidney cell. The cell is contacted in vitro, ex vivo or in vivo.

Alternatively, the cell is contacted with a cytokine in an amount sufficient to increase expression or activity of a glycoprotein or glycolipid. The glycoprotein or glycolipid is cytosolic or cell membrane protein or lipid. By increased expression or activity of a glycoprotein or a glycolipid it is meant that the cell expresses a greater amount of the glycoprotein or a glycolipid as compared to a cell that has not been contacted with the cytokine or that the affinity of the cell for the ligand of the glycoprotein or a glycolipid is increased. For example, the treated cell has an increase affinity for a selectin. Affinity is measured by methods known in the art.

For example, cell surface expression of a selectin ligand, or a lewis antigen is increased following treatment of the cell with the cytokine. Selectins include E-selectin, L-selectin or P-selectin. The selectin ligands include, for example, MAdCAM1, CD334, PSGL-1, CD24, ESL-1 or the VIM-2 epitope. Preferably, the selectin ligand is, a hematopoietic cell E-/L-selectin ligand (HCELL) or a 65 kDa E-selectin ligand described herein. Lewis antigens include $Le^a$ epitope, the $Le^b$ epitope, $Le^x$ or the $Le^y$ epitope. The Lewis antigen is sialyated. Preferably, cell surface expression of a $Le^x$ epitope or the siayl $Le^x$ epitope is increased following cytokine treatment of the cell. Exemplary, $Le^x$ antigens include CD15 and CD15s.

The invention also provides methods to treat or alleviate the symptoms of a variety of disorders. For example, cells produced by the methods of the invention can be administered to a subject to treat a tissue injury or as part of a stem cell transplant protocol. The cells treated according to the method of the invention have an increased regenerative/engraftment potential and are useful for a variety of therapeutic methods including, tissue repair, tissue regeneration, and tissue engineering. By increased regenerative/engraftment potential it is meant that the cell has a greater survival rate after transplantation as compared to an untreated cell.

For example, the cells treated according to the methods of the invention are useful in bone regeneration, cardiac regeneration, vascular regeneration, neural regeneration and the treatment of ischemic disorders. Ischemic conditions include, but are not limited to, limb ischemia, congestive heart failure, cardiac ischemia, kidney ischemia, ESRD, stroke, and ischemia of the eye. The cells are administered to mammalian subjects, to effect tissue repair or regeneration. The cells are administered allogeneically or autogeneically.

The cell can be of mesodermal, ectodermal or endoderamal origin. Preferably, the cell is a stem cell. More preferably the cell is of mesodermal origin. For example, the cell is a hematopoietic progenitor cell.

Included in the invention is a method of increasing the engraftment potential of a cell by providing a cell and contacting said cell with one or more cytokines that increases cell-surface expression or activity of a selectin ligand, e.g. HCELL on the cell. The invention further provides a method of increasing levels of engrafted stem cells in a subject, e.g., human, by administering to the subject a cytokine that increases cell-surface or expression of a selectin ligand on one or more stem cells in the subject. The cytokine can be administered in vivo, ex vivo or in vitro.

The subject is preferably a mammal. The mammal can be, e.g., a human, non-human primate, mouse, rat, dog, cat, horse, or cow. Additionally, the subject suffers from or is at risk of developing a hematopoietic disorder, e.g, leukemia, cancer, or a tissue injury. A mammal suffering from or at risk of developing a hematopoietic disorder, e.g, leukemia, cancer, or tissue injury can be identified by the detection of a known risk factor, e.g., gender, age, prior history of smoking, genetic or familial predisposition, attributed to the particular disorder. Alternatively, a mammal suffering from or at risk of developing a hematopoietic disorder, e.g, leukemia, or tissue injury can be identified by methods known in the art to diagnosis a particular disorder.

Pharmaceutical Administration and Dosage Forms

The described cells can be administered as a pharmaceutically or physiologically acceptable preparation or composition containing a physiologically acceptable carrier, excipient, or diluent, and administered to the tissues of the recipient organism of interest, including humans and non-human animals. Cell-containing compositions can be prepared by resuspending the cells in a suitable liquid or solution such as sterile physiological saline or other physiologically acceptable injectable aqueous liquids. The amounts of the components to be used in such compositions can be routinely determined by those having skill in the art.

The cells or compositions thereof can be administered by placement of the cell suspensions onto absorbent or adherent material, i.e., a collagen sponge matrix, and insertion of the cell-containing material into or onto the site of interest. Alternatively, the cells can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the cells can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

Consistent with the present invention, the cell can be administered to body tissues, including liver, pancreas, lung, salivary gland, blood vessel, bone, skin, cartilage, tendon, ligament, brain, hair, kidney, muscle, cardiac muscle, nerve, skeletal muscle, joints, and limb.

The number of cells in a cell suspension and the mode of administration may vary depending on the site and condition being treated. As non-limiting examples, in accordance with the present invention, about $35-300 \times 10^6$ cells are injected to effect tissue repair. Consistent with the Examples disclosed herein, a skilled practitioner can modulate the amounts and methods of cell-based treatments according to requirements, limitations, and/or optimizations determined for each case.

The preferred suspension solution is Multiple Electrolyte Injection Type 1 (USP/EP). Each 100 mL of Multiple Electrolyte Injection Type 1 contains 234 mg of Sodium Chloride, USP (NaCl); 128 mg of Potassium Acetate, USP ($C_2H_3KO_2$); and 32 mg of Magnesium Acetate Tetrahydrate (Mg $(C_2H_3O_2)_2.4H_2O$). It contains no antimicrobial agents. The pH is adjusted with hydrochloric acid. The pH is 5.5 (4.0 to 8.0). The Multiple Electrolyte Injection Type 1 is preferably supplemented with 0.5% human serum albumin (USP/EP). Preferably, the cell pharmaceutical composition is stored at 0-12° C., unfrozen.

Indications and Modes of Delivery for Cells

Cells may be manufactured and processed for delivery to patients using the described methods where the final formulation is the cells with all culture components substantially removed to the levels deemed safe by the FDA. It is critical for the cells to have a final viability greater than 70%, however the higher the viability of the final cell suspension the more potent and efficacious the final cell dose will be, and the less cellular debris (cell membrane, organelles and free nucleic acid from dead cells), so processes that enhance cell viability while maintaining the substantially low culture and harvest components, while maintaining closed aseptic processing systems are highly desirable.

Limb Ischemia

It has been demonstrated that bone marrow-derived cells are used for vascular regeneration in patients with critical limb ischemia, peripheral vascular disease, or Burger's syndrome. The cells delivered to patients with ischemic limbs, and have been shown to enhance vascular regeneration. Cells are delivered to patients by creating a cell suspension and removing the cells from the supplied bag or vial in which they are delivered. A syringe is used to remove the cell suspension, and then smaller 0.25 ml to 1 ml individual injection volumes are loaded from the main syringe using a syringe adaptor, and then several individual injection volumes are delivered via intramuscular injection to the site of limb ischemia and where vascular formation is required. The cells may be delivered through a wide range of needle sizes, from large 16 gauge needles to very small 30 gauge needles, as well as very long 28 gauge catheters for minimally invasive procedures. Alternatively, the cells may also be delivered intravascularly and allowed to home to the site of ischemia to drive local tissue regeneration.

Cardiac Regeneration

There are a variety of modes of delivery for driving cardiac tissue regeneration. The cells are delivered intra-vascularly and allowed to home to the site of regeneration. Alternatively, the cells are also be delivered directly into the cardiac muscle, either epicardially or endocardially, as well as transvascularly. The cells may be delivered during an open-chest procedure, or via minimally invasive procedures such as with delivery via a catheter. The cells are delivered to these patients by creating a cell suspension and removing the cells from the supplied bag or vial in which they are delivered. A syringe is used to remove the cell suspension, and then smaller 0.25 ml to 1 ml individual injection volumes are loaded from the main syringe using a syringe adaptor, and then several individual injection volume are delivered via intramuscular injection to the site of cardiac ischemia and where vascular formation is required. The cells may be delivered through a wide range of needle sizes, from large 16 gauge needles to very small 30 gauge needles, as well as very long 28 gauge catheters for minimally invasive procedures.

Spinal Cord Regeneration

There are a variety of ways that cells are used for regeneration after spinal cord injury (SCI). Cells may be injected directly into the site of SCI, seeded onto a matrix (chosen from the list below for bone regeneration) and seeded into re-sected spinal cord or placed at the site such that the cells may migrate to the injury site. Alternatively, the cells are delivered intravascularly and allowed to home to the site of injury to drive local tissue regeneration.

There are a variety of other applications where the cells may be delivered locally to the tissue via direct injection, seeding onto a matrix for localized delivery, or delivered via the vascular system allowing for cells to home to the site of injury or disease. These diseases are limb ischemia, congestive heart failure, cardiac ischemia, kidney ischemia, end stage renal disease, stroke, and ischemia of the eye.

Orthopedic Indications for Bone Regenerations

Cells have been used successfully in bone regeneration applications in humans. Optionally, cells are mixed with 3D matrices to enhance delivery and localization at the site where bone regeneration is required. The three-dimensional matrices come in a range of physical and chemical forms, and viscous or gelled binding materials may also be added to aid handling and delivery properties.

Three dimensional matrices include for example, demineralized bone particles, mineralized bone particles, synthetic ceramics of the calcium phosphate family such as alpha tricalcium phosphates (TCP), beta TCP, hydroxyappatites, and complex mixtures of these materials. Other matrices include, for example, collagen-based sponges, polysaccharide-based materials such as hyaluronan and alginates, synthetic biodegradable polymeric materials such as poly-lactides, polyglycolides, poly-fumarates, poly-ethylene glycol, co-polymers of these as well as other materials known in the art.

Any of the matrices used with cells may be processed into different physical forms that are common in the art for tissue regeneration applications. These physical forms are open and closed pore foams and sponges, fiber-based woven or non-woven meshes, or small particles ranging from nano-particles to micron-sized particles (1 micrometer-1000 micrometers) and macro-particles in the millimeter size scale. The small particles also often have an open porosity, with nanopores aiding in nutrient and metabolite transport and micropores providing pores large enough to facilitate cell seeding and tissue integration.

When the matrices used for cell delivery are small particles delivered to wound sites, at times viscous materials or gels are used to bind the particles that aid in materials handling and delivery, as well as helping to keep the particles and the cells localized at the site after placement. Viscous binding materials include for example, hyaluronan, alginates, collagens, poly ethylene glycols, poly fumarates, blood clots and fibrin-based clots, as well as mixtures of these materials, either in the form of viscous fluids to soft or hard hydrogels. Other viscous materials and hydrogels are known in the art In various embodiments, cells are delivered with TCP, demineralized bone, and mineralized bone particles in sizes ranging from 200 micrometers to 5 millimeters, depending on the specific application. Optionally, these materials are bound with fibrin-based clots made from autologous freshly prepared plasma from the patient. Other fibrin clots or different hydrogels, or matrix materials common may also be used.

Generally, cells are mixed with the matrices just prior to surgery when used for bone regeneration. For long-bone regeneration, typically the area of bone non-union is opened by the surgeon, and the necrotic bone is removed. The non-unioned bone or area where bone is needed may or may not be de-corticated by the surgeon to allow bleeding at the site, at which point the cell-matrix mixture is placed by the surgeon between the bones where regeneration will occur. This mixture of the cells and matrix drive tissue regeneration with the physical matrix guiding the location of bone regeneration and the cells providing the tissue repair stimulus for driving angiogenesis, would healing, and bone regeneration. The remaining cell/matrix mixture is optionally placed around the fracture line after any orthopedic hardware has been placed such as plates, rods, screws or nails.

Methods of Reducing Inflammation

Inflammation is inhibited (e.g., reduced) by administering to tissue a selectin inhibitor. Tissues to be treated include any tissue subject to inflammation such as a gastrointestinal tissue, e.g., intestinal tissue, a cardiac tissue, a muscle tissue, an epithelial tissue, an endothelium tissue, a vascular tissue, a pulmonary tissue, a dermal tissue, or a hepatic tissue. For example, the tissue is an epithelial tissue such as an intestinal epithelial tissue, pulmonary epithelial tissue, dermal tissue (i.e., skin), or liver epithelial tissue.

Inhibition of inflammation is characterized by a reduction of redness, pain and swelling of the treated tissue compared to a tissue that has not been contacted with a selectin inhibitor. Tissues are directly contacted with an inhibitor. Alternatively, the inhibitor is administered systemically. Selectin inhibitors are administered in an amount sufficient to decrease (e.g., inhibit) leukocyte-endothelial interaction. The selectin inhibitor is administered to a subject prior to, during or after receiving G-CSF therapy. An inflammatory response is evaluated by morphologically by observing tissue damage, localized redness, and swelling of the affected area. Alternatively, an inflammatory response is evaluated by measuring c-reactive protein, or IL-1 in the tissue or in the serum or plasma. Efficaciousness of treatment is determined in association with any known method for diagnosing or treating the particular inflammatory disorder. Alleviation of one or more symptoms of the inflammatory disorder indicates that the compound confers a clinical benefit.

The methods described herein lead to a reduction in the severity or the alleviation of one or more symptoms of an inflammatory disorder. The inflammatory disorder is acute or chronic. For example, the methods described herein reduce the severity of vascular and inflammatory complications associated with G-CSF therapy. Complications associated with G-CSF therapy include, for example, respiratory distress syndrome, angina pectoris, myocardial infarct, cutaneous leukocytoclastic vasculitis, arthritis, precipitate sickle cell vaso-occlusion, and cardiac ischemia. Disorders are diagnosed and or monitored, typically by a physician using standard methodologies.

The subject is preferably a mammal. The mammal can be, e.g., a human, non-human primate, mouse, rat, dog, cat, horse, or cow. The subject suffers from a disorder in which G-CSF therapy is indicated. For example, the subject is receiving a hematopoietic stem cell transplant.

A selectin inhibitor is a compound meant a compound that inhibits or reduces selectin-ligand interaction. Selectin inhibitors are known in the art such as those described in U.S. Pat. No. 5,728,685 (the contents of which are incorporated herein by reference) or are identified using methods described herein. The selectin inhibitor is, for example, a small molecule, and antisense nucleic acid, a short-interfering RNA, or a ribozyme.

EXAMPLES

Example 1

General Methods

Materials: G-CSF mobilized peripheral blood (MPB) was obtained from pheresis products of donors for clinical HSCT at Brigham and Women's Hospital/Dana Farber Cancer Institute (Boston, Mass.). G-CSF MPB leukocytes (ML) were isolated from buffy coat of dextran sedimentated whole blood, followed by hypotonic lysis to remove contaminating red cells. Mononuclear fraction of these cells (ML-M) was isolated by Ficoll-Hypaque (1.077 g/ml; Sigma Aldrich) density gradient centrifugation. Native (unmobilized) peripheral blood was obtained from consenting healthy volunteers, and NL (buffy coat) were isolated using dextran sedimentation as for ML. Peripheral blood mononuclear cells (PBMC) were isolated by Ficoll-Hypaque density gradient centrifugation. Polymorphonuclear leukocytes (PMN) were isolated by dextran sedimentation followed by collecting the cell pellet after Ficoll-Hypaque density gradient centrifugation. Contaminated red cells were removed by hypotonic lysis.

Normal human bone marrow (BM) cells were isolated from human BM harvest material (Massachusetts General Hospital, Boston, Mass.). Red cells were separated using dextran sedimentation method. The leukocyte-rich supernatant was subjected to a two-step discontinuous Percoll (Amersham Pharmacia Biotech; Piscataway, N.J.) density gradient centrifugation (1.065 g/ml and 1.080 g/ml; 1000 g for 20 min at 4° C.). This resulted in separation of BM cells into three different "bands" according to myeloid cell maturity[50]. The cells with least density found at the upper band ("Band 1") contained early immature cells (myeloblasts and promyelocytes), "Band 2" contained late immature cells (primarily myelocytes and metamyelocytes), and "Band 3" contained the most mature leukocytes (predominantly band and segmented neutrophils) as well as some contaminating red cells, which were subsequently removed by hypotonic lysis. The cells in different bands were collected, washed and used for further studies. In some instances, BM mononuclear cells (BM-MNC) were isolated by Ficoll-Hypaque density gradient centrifugation. CD34+/lineage—subpopulation was isolated from BM-MNC using a negative cell selection Stem-Sep™ human progenitor enrichment cocktail (Stem Cell Technologies Inc.); CD34+ cells were then further isolated by positive selection using anti-CD34 immunomagnetic beads (Miltenyi Biotech.), routinely resulting in populations of >98% CD34+ cells.

All human samples were obtained and used in accordance with the procedures approved by the Human Experimentation and Ethics Committees of Partners Cancer Care Institutions (Massachusetts General Hospital, Brigham and Women's Hospital and Dana Farber Cancer Institute (Boston, Mass.)).

Antibodies and E-selectin chimera:

The following antibodies were from BD Pharmingen (San Diego, Calif.): function blocking murine anti-human E-selectin (68-5411; $IgG_1$), rat anti-human CLA (HECA-452; IgM), murine anti-human PSGL-1 (KPL-1; $IgG_1$), purified and fluorescein isothiocynate (FITC)-conjugated murine anti-human L-selectin (DREG-56; $IgG_1$), murine anti-human CXCR4 (12G5; $IgG_{2a}$), murine anti-human CD29 (HUTS-21; $IgG_{2a}$), mouse $IgG_1$,κ isotype, mouse $IgG_{2a}$ isotype, rat IgG isotype, rat IgM isotype, FITC-conjugated goat anti-mouse Ig and FITC-conjugated goat anti-rat IgM. Rat anti-human CD44 (Hermes-1; $IgG_{2a}$) was a gift of Dr. Brenda Sandmaier (Fred Hutchinson Cancer Research Center; Seattle, Wash.). Murine anti-human CD44 (F10-44-2; mIgM), phycoerythrin (PE)-conjugated strepavidin, alkaline phosphatase (AP)-conjugated anti-rat IgM, anti-rat IgG, anti-mouse Ig, and anti-human Ig were from Southern Biotechnology Associates (Birmingham, Ala.). Recombinant murine E-selectin/human Ig chimera (E-Ig) and murine anti-human CD44 (2C5; $IgG_{2a}$) were from R&D Systems (Minneapolis, Minn.). Murine anti-human PSGL-1 (PL-2; $IgG_1$), murine anti-human CD11a (25.3, $IgG_1$), function blocking murine anti-human CD18 (7E4, $IgG_1$), murine anti-human CD49d (HP2/1, $IgG_1$), purified and PE-conjugated murine anti-human CD34 (QBEND10; $IgG_1$) and PE-conjugated mouse $IgG_1$,κ isotype were from Coulter-Immunotech (Miami, Fla.). Function blocking rat anti-murine E-selectin (9A9; $IgG_1$) was a kind gift of Drs. Barry Wolitzky (CHIRON BioPharma Research; Emeryville, Calif.) and Klaus Ley (University of Virginia; Charlottesville, Va.)[26,27].

Cell culture and treatment of HUVEC:

HUVEC were obtained from the tissue culture core facility at Brigham and Women's Hospital's Pathology Department and were cultured in M199 supplemented with 15% FBS, 5 units/ml heparin, 50 µg/ml endothelial growth factor, 100 units/ml penicillin and 100 µg/ml streptomycin. For adhesion assays, the HUVEC were cultured at the center of 100-mm tissue culture dishes (BD Falcon; Franklin Lakes, N.J.) coated with 10 µg/ml human plasma fibronectin (Sigma). All experiments were performed with confluent HUVEC monolayers. To stimulate expression of endothelial adhesion molecules including E-selectin, HUVEC were pre-treated with 20 ng/ml of recombinant human TNF-α (endotoxin<0.1 ng/µg TNF-α; Research Diagnostics, Inc; Concord, Mass.) or 2 ng/ml of recombinant human IL-1β (endotoxin<0.1 ng/µg IL-1β; Research Diagnostics, Inc.) for 4-6 hrs prior to use in the adhesion studies.

Human hematopoietic KG1a cell line (ATCC; Manassas, Va.) was cultured as described previously[28,39]. Chinese hamster ovary cells (CHO) stably transfected with full-length cDNA encoding human E-selectin (CHO-E cells) or human P-selectin (CHO-P cells) and mock-transfected CHO cells (CHO-mock)[29] were cultured in MEM supplemented with 10% FBS, 1% sodium pyruvate, 1% non-essential amino acids, 100 units/ml penicillin and 100 µg/ml streptomycin.

Parallel plate flow chamber adhesion assays:

A tissue culture dish containing confluent HUVEC monolayer or CHO cells was loaded into a parallel plate flow chamber (Glycotech; Gaithersburg, Md.). The flow chamber was mounted on an inverted microscope connected to a videocamera, VCR, and monitor. The field of view was standardized to the mid-point of the flow chamber. After a brief rinse with HBSS/10 mM HEPES/2 mM $CaCl_2$ (assay buffer), ML or NL ($1\times10^6$ cells/run in assay buffer) were drawn over the HUVEC monolayer or CHO cells at a shear stress of 1.5 dyne/cm$^2$ or 1 dyne/cm$^2$ respectively. In certain experiments, TNF-α-stimulated HUVEC or CHO-E cells were treated with anti-human E-selectin mAb, 68-5411. The mAb treated HUVEC or CHO-E cells were then incubated at 37° C. for 15 min prior to use in adhesion assays. In other experiments, ML were treated with anti-human L-selectin mAb, Dreg-56 or anti-human CD18 (β2 integrin) mAb, 7E4 or anti-human CD29 (β1 integrin) mAb, HUTS-21 or mouse $IgG_{1,k}$ at 4° C. for 15 min prior to use in adhesion assays. Primary tethering[49] was determined by quantifying the number of ML or NL that attached (i.e., interacted) from the free stream directly onto HUVEC monolayer or CHO cells during the first 2 minutes of flow. Secondary attachments (i.e., flowing leukocytes interacting with an already adherent leukocyte on HUVEC monolayer or CHO cells) or leukocytes that rolled into the field of observation from the upstream region were not counted. Average rolling velocity, a quantitative measure of selectin binding strength, was computed (using Scion Image) as the displacement by the centroid of the cell divided by the time interval of observation, 5 sec.

In vivo imaging of cellular trafficking:

All studies were performed in accordance with NIH guidelines for the care and use of animals and under approval of the Institutional Animal Care and Use Committees of Partners Affiliated Institutions and the Harvard Medical School. Groups of C57BL/6 mice received intradermal injection of 200 ng/ml of TNF-α in a volume of 10 µl into the right ear. As a control, the left ear pinnae received intradermal injection of PBS. Six hours later, an intravenous catheter was inserted into the tail vein of anesthetized mice. The anesthetized mice were placed in a heated tube on the stage of a video rate scanning laser confocal microscope platform[25]. To image the vasculature, the ears of mice were placed on a coverslip and high-resolution images with cellular details was obtained through the intact mouse skin at depths of up to 250 µm from the surface using a Olympus 60X 1.2NA water immersion objective lens. For cell tracking, animals received $5\times10^6$ of DiD labeled (Molecular Probes) ML or NL suspended in 200 µl sterile saline (tail-vein injection), while on the stage, and their interaction with ear vasculature was viewed using in vivo confocal microscopy. DiD was excited with a 656 nm diode laser and detected with a photomultiplier tube through a 695+/−27.5 nm bandpass filter (Omega Optical). The system operates at a user-selectable frame rate from 15-30 fps. The images are simultaneously recorded by a digital video recorder (Canon) and captured by a Macintosh computer equipped with a Scion LG-3 board for frame averaging[25]. In some experiments, mice were treated with 70 µg of mAb 9A9 for 1 hr. prior to injection of leukocytes. Average rolling velocity was computed (using ImageJ) as the displacement by the centroid of the cell divided by the time interval of observation.

OSGE treatment:

ML ($10\times10^6$ cells/ml) were treated at 37° C. for 1 hr with 30 µg/ml OSGE (Cedarlane Laboratories, Ontario, Canada). Following the incubation, the cells were washed and divided proportionately for use in flow cytometry, Western blot analysis, and parallel plate flow chamber adhesion assays.

G-CSF treatment:

For in vitro G-CSF treatment, isolated subsets of BM cells ($1\times10^6$ cells/ml) were cultured at 37° C. for 72 hr in the presence of recombinant human G-CSF (10 ng/ml in RPMI, 10% FBS; Amgen, Thousand Oaks, Calif.)); PBS diluent was used for control (untreated) cells. Note that the in vitro dose of G-CSF utilized is well within the expected levels in human serum/extracellular fluids (after a single subcutaneous dose of 5 or 10 µg/kg, peak serum levels range from ~15.1 to ~100.5 ng/ml)[44,45]. In all experiments, L-selectin expression was determined by flow cytometry on untreated and G-CSF-treated cells to test the efficacy of G-CSF treatment. At the end of the culture period, equal numbers of untreated and G-CSF treated cells were divided proportionately for use in flow cytometry, Western blot analysis, RT-PCR and parallel plate flow chamber adhesion assays. For Western blot analysis, cells were lysed in 2% NP-40 in Buffer A (consisting of 150 mM NaCl, 50 mM Tris-HCl pH 7.4, 1 mM EDTA, 0.02% sodium azide, 20 mg/ml PMSF and 1 complete protease inhibitor cocktail tablet/100 ml buffer). The lysate was used immediately or stored at −20° C. for later use.

Membrane preparations, SDS separation and Western blots:

Membrane proteins of purified ML-M, ML-G, PMN, or PBMC were isolated as described previously[28,39]. Membrane protein suspensions were aliquoted and stored at −20° C. For SDS-PAGE and Western blotting, membrane preparations were diluted in reducing sample buffer, boiled and then separated on 4-20% or 7.5% Criterion Tris-HCl SDS-PAGE gels (Bio-Rad Laboratories). Resolved membrane proteins were transferred to Sequi-blot polyvinylidene diflouride (PVDF) membrane (Bio-Rad Laboratories) and blocked with heat inactivated FBS. Blots were incubated with primary antibodies or E-Ig (each at 1 µg/ml). Appropriate isotype control immunoblots (each at 1 µg/ml) were performed in parallel to evaluate nonspecific binding to protein bands. After extensive washing with TBS/0.1% Tween 20, blots were incubated with appropriate alkaline phosphatase (AP)-conjugated secondary antibodies (1:1000). Western Blue AP substrate (Promega, Madison, Wis.) was used to develop the blots.

Immunoprecipitation Studies:

Membrane proteins of ML-M were incubated with immunoprecipitating antibodies or E-Ig, or with appropriate isotype controls and then incubated with Protein G-agarose. Immunoprecipitates were washed extensively using Buffer A containing 2% NP-40, 1% SDS. E-Ig precipitated material was washed extensively with Buffer A without EDTA containing 2% NP-40 and 2 mM $CaCl_2$. All immunoprecipitates were diluted in reducing sample buffer, boiled, then subjected to SDS-PAGE, transferred to PVDF membrane, and immunostained with HECA-452 or appropriate mAbs.

In some experiments, the surface proteins on ML-M and KG1a cells were biotinylated using EZ-Link® NHS-$PEO_4$-Biotin (Pierce Biotechnology, Inc.; Rockford, Ill.). An aliquot of cells ($1\times10^6$ cells) was removed and the efficiency of biotinylation determined using flow cytometry. The remaining cells were solubilized in Buffer A containing 2% NP-40. L-selectin was immunoprecipitated using polyclonal rabbit anti-human L-selectin antiserum (prepared by Covance, Princeton, N.J.). Control immunoprecipitation was performed in parallel using rabbit pre-immune serum (Covance). Immunoprecipitated proteins were diluted in reducing sample buffer, boiled, then subjected to SDS-PAGE, transferred to PVDF membrane and immunostained with horseradish peroxidase (HRP) conjugated strepavidin (1:500; Dako Cytomation; Carpinteria, Calif.). Vector Nova Red HRP substrate (Vector Laboratories; Burlingame, Calif.) was used to develop the blots.

Blot rolling assays:

The blot rolling assay has been described previously[29]. CHO-E were washed in PBS, and resuspended to $2 \times 10^6$ cells/ml in assay buffer/10% glycerol. Western blots of ML-M membrane preparations stained with HECA-452 were rendered translucent by immersion in assay buffer/10% glycerol. These blots were then placed in the parallel plate flow chamber, and CHO-E were perfused into the chamber at a shear stress of 0.6 dyne/cm$^2$; an adjustment in the volumetric flow rate was made to account for the increase in viscosity due to the presence of 10% glycerol in the assay buffer. Molecular weight standards (SeeBlue® Plus2 prestained molecular weight standard; Invitrogen Corporation; Carlsbad, Calif.) were co-electrophoresed on adjacent lanes and served as a guide to aid placement of the flow chamber over the stained bands of interest. The number of tethering and rolling CHO-E was tabulated as function of the molecular weight region and compiled into an adhesion histogram. Negative controls were prepared by adding 10 mM EDTA to the assay buffer to chelate Ca$^{2+}$ required for binding or treating CHO-E with anti E-selectin mAb, 68-5411, at 4° C. for 15 min. prior to use in adhesion assays.

Flow cytometry:

Aliquots of ~2-5×10$^5$ cells were washed with PBS, 2% FBS and incubated with primary mAbs. Subsequently, the cells were washed and incubated with species and isotype matched FITC- or PE-labeled polyclonal antibodies. Following this incubation, the cells were washed and FITC or PE fluorescence of cells was determined using a Cytomics FC 500 MPL flow cytometer (Beckman Coulter Inc., Fullerton, Calif.).

RT-PCR:

Total cellular RNA was isolated from equal numbers of NL and ML or untreated or G-CSF-treated human BM cells using Trizol® LS reagent (Life Technologies, Inc.) according to the manufacturer's protocol. The isolated RNA was quantified by spectrophotometric absorbance readings at 260 nm. Equal amounts of RNA were then taken and used as templates for RT-PCR with Titan™ One Tube RT-PCR System (Roche Molecular Biochemicals) and the following primers: ST3Gal IV, sense CTC TCC GAT ATC TGT TTT ATT TTC CCA TCC CAG AGA GAA GAA GGA G (SEQ ID NO:1) and antisense GAT TAA GGT ACC AGG TCA GAA GGA GGT GAG GTT CTT (SEQ ID NO:2); FucT-VII, sense CCC ACC GTG GCC CAG TAC TAC CGC TTC T (SEQ ID NO:3) and antisense CTG ACC TCT GTG CCC AGC CTC CCG T (SEQ ID NO:4); FucT-IV, sense CGG GTG TGC CAG GCT GTA CAG AGG (SEQ ID NO:5) and antisense TCG GGA ACA GTT GTG TAT GAG ATT (SEQ ID NO:6); GAPDH sense GAA GGT GAA GGT CGG AGT C (SEQ ID NO:8) and antisense GAA GAT GGT GAT GGG ATT TC (SEQ ID NO:9).

A total of 30 cycles were found to be below the plateau phase of amplification for all primers giving an accurate reflection of the relative concentration of mRNA. Optical PCR conditions were 94° C. for 2 min, 60° C. for 45 sec., and 72° C. for 1 min on a PTC-200 Peltier Thermal cycler (MJ Research). Amplified bands were visualized after 1% agarose (Sigma Aldrich) gel electrophoresis of the PCR products. Analysis of digital images of amplified bands was done using Kodak software. Mean intensities were determined of fixed size regions set over each band. The background intensity for each lane was subtracted from mean intensity in the same lane to arrive at net intensity. The net intensity of the specific band was then normalized to the net intensity of GAPDH control.

Statistics:

When comparing two means, statistical analyses were done by unpaired Student's t-test of the means. P values<0.05 were considered statistically significant. Unless stated otherwise, all error bars represent standard error of mean.

Example 2

ML Possess Enhanced Binding to E-Selectin Relative to NL

Figure 1A:
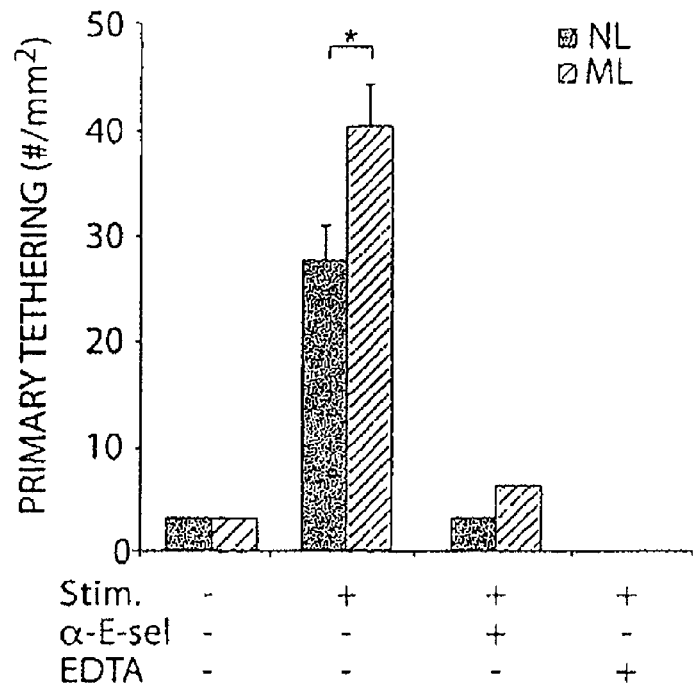
FIGS. 1 A-G illustrates ML possess enhanced binding to E-selectin relative to native leukocytes (NL). Human umbilical vein endothelial cells (HUVEC) were stimulated with TNF-α for 4-6 hrs. Subsequently, ML or NL were perfused in a parallel plate apparatus over HUVEC at 1.5 dyne/cm$^2$. In certain instances, HUVEC were pretreated with a mAb to E-selectin prior to use in adhesion assays. (A) Primary tethering and (B) average rolling velocity of ML or NL on HUVEC was determined. "Stim" indicates stimulation (+) or no stimulation (−) of HUVEC with TNF-α for 4-6 hours prior to the assay; α-E-sel indicates pretreatment (+) or no pretreatment (−) of HUVEC with a function blocking mAb to E-selectin, (68-5411); EDTA indicates presence (+) or absence (−) of 5 mM EDTA in the assay buffer. Values are means±SE of n≥4 different runs. * indicates statistically significant difference (p<0.05). C-D Are bar graph results of ML or NL perfused over CHO-E at 1 dyne/cm$^2$. In certain instances, CHO-E were pretreated with a function blocking mAb to E-selectin prior to use in adhesion assays. (C) Primary tethering and (D) average rolling velocity of ML or NL on CHO-E was determined. α-E-sel indicates pretreatment (+) or no pretreatment (−) of CHO-E with a function blocking mAb to E-selectin, (68-5411); EDTA indicates presence (+) or absence (−) of 5 mM EDTA in the assay buffer; Values are means±SE of n≥5 different runs. * indicates statistically significant difference (p<0.05). E-G Show results of ML and NL that were treated with DiD ex vivo and injected into the tail vein of mice 5-6 hours after stimulation of one ear locally with TNF-α. (E) Represents the average rolling velocity of ML or NL on inflamed vascular endothelium in TNF-α-treated ears of mice. Values represent means±SE of 10-20 leukocytes per mouse with n=3 for each group. (F) Shows representative images of the adhesive interactions of NL (top) and ML (bottom) with inflamed vascular endothelium in TNF-α-treated ears of two separate mice. Minimal adhesive interactions were observed in control PBS-treated ear (not shown). (G) is a bar graph showing adherent leukocytes per field of view. Values represent means±SE of 15-25 fields of view per mouse with n=3 for each group. * indicates statistically significant difference (p<0.05).
Figure 1B:
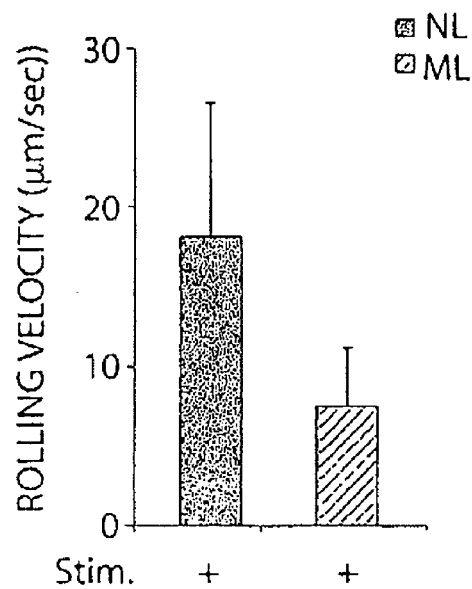
Figure 1C:
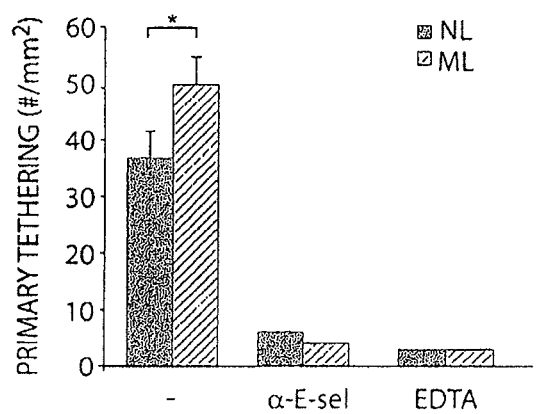
Figure 1D:
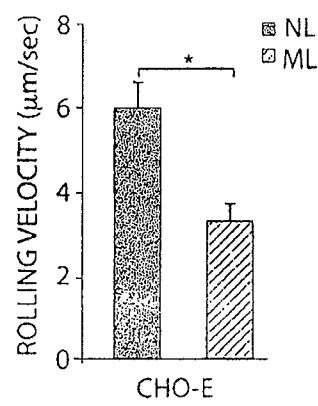
Figure 7:
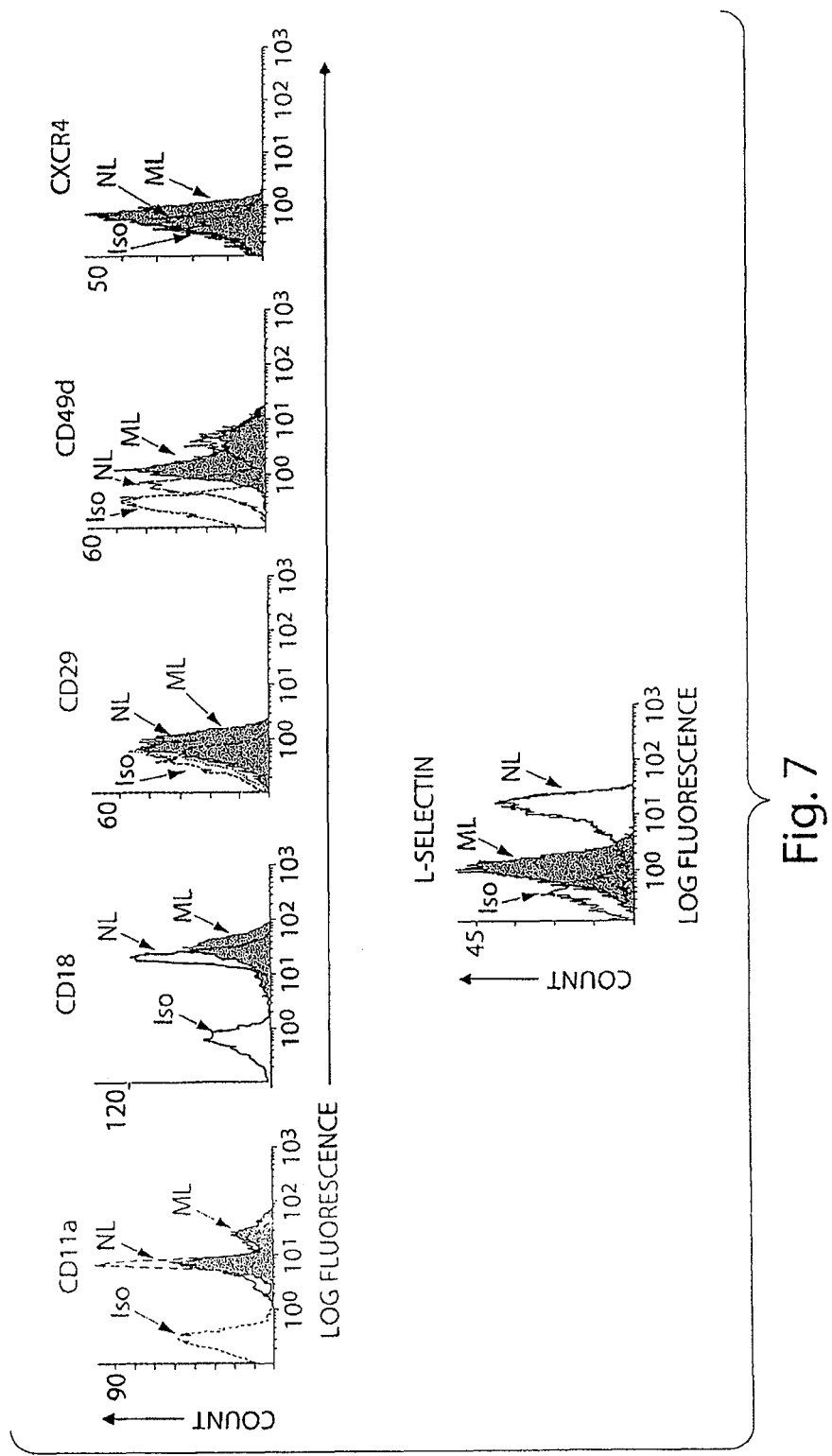
FIG. 7 illustrates that there is no distinct difference in the surface expression of integrin-type homing receptors (e.g., LFA-1 (CD11a/CD18; αLβ2) and VLA-4 (CD49d/CD29; α4β1)) and chemokine receptor CXCR4 on ML and NL. CD11a, CD18, CD29, CD49d and CXCR4 expression was determined on ML and NL using flow cytometry. mAbs 25.3, 7E4, HUTS-21, HP2/1 and 12G5 were used to determine expression of CD11a, CD18, CD29, CD49d and CXCR4, respectively. $mIgG_{1,k}$ served as an isotype control for 25.3, 7E4 and HP2/1 and $mIgG_{2a}$ served as an isotype control for HUTS-21 and 12G5. Results shown are representative of 2 separate experiments.

We analyzed adhesive interactions of ML and NL on TNF-α-stimulated human umbilical vein endothelial cells (HUVEC) in a parallel plate flow chamber assay. Under hemodynamic flow conditions (1.5 dyne/cm$^2$), ML displayed markedly enhanced E-selectin-mediated and Ca$^{2+}$-dependent primary tethering on stimulated HUVEC compared to NL (FIG. 1a). Moreover, ML rolled distinctly slower than NL on stimulated HUVEC (FIG. 1b). Because activated integrins support deceleration of cells in flow, we measured the surface expression of activation-dependent epitopes of integrins LFA-1 (CD11a/CD18;$\alpha_L\beta_2$) and VLA-4 (CD49d/CD29; $\alpha_4\beta_1$), and of chemokine-receptor CXCR4 on ML and NL. Flow cytometry revealed no difference in the expression of these molecules (FIG. 7a) suggesting that the marked decrease in rolling velocity of ML was primarily due to their increased capacity to engage endothelial E-selectin. To further characterize the enhanced E-selectin binding capacity of ML, we examined the adhesion of ML and NL on Chinese hamster ovary cells transfected with human E-selectin (CHO-E). ML displayed significantly enhanced E-selectin-mediated and Ca$^{2+}$-dependent primary tethering on CHO-E (FIG. 1c). Furthermore, the rolling velocity of ML on CHO-E was significantly lower than that of NL (FIG. 1d).

Figure 1E:
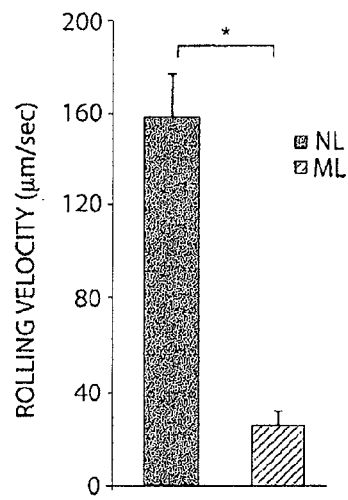
Figure 1F:
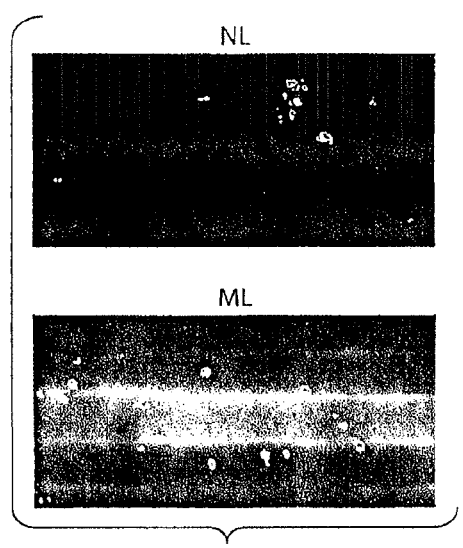
Figure 1G:
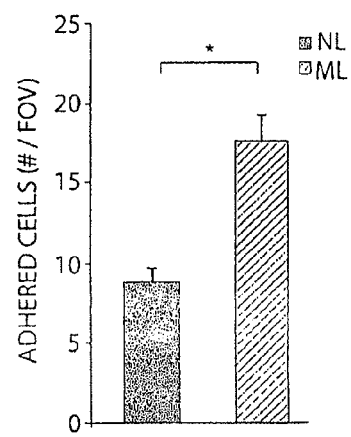

To assess whether the observed enhanced E-selectin binding of ML in vitro could have a meaningful physiologic effect in vivo, we utilized TNF-α-induced murine ear inflammation model and employed dynamic real-time intravital confocal microscopy[25] to visualize the adhesive interactions of ML and NL with inflamed ear vasculature. Compared to NL, ML displayed significantly slower rolling (FIG. 1e) and significantly enhanced adhesion (FIGS. 1f and 1g) to vascular endothelium within the TNF-α-treated ear. A function blocking mAb to murine E-selectin, 9A9[26,27], prominently increased the rolling velocity and diminished leukocyte adhesion to inflamed endothelium, highlighting a critical role for vascular E-selectin/leukocyte E-selectin ligand interactions in mediating this enhanced adhesion. Collectively, these data demonstrate that ML possess heightened adhesive interactions with endothelium mediated by enhanced binding to E-selectin.

Example 3

Figure 2A:
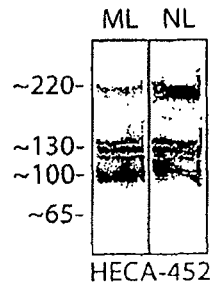
FIGS. 2A-E illustrates how ML express multiple HECA-452-reactive E-selectin glycoprotein ligands. (A) Shows HECA-452 blots of cell lysate from (unfractionated) buffy coat of ML or NL resolved on a reducing 4-20% SDS-PAGE gel. (B) Shows HECA-452 blots of membrane preparations of mononuclear fraction of G-CSF mobilized peripheral blood (MPB) leukocytes (20 µg; ML-M), G-CSF mobilized granulocytes (40 µg; ML-G); native peripheral blood mononuclear cells (40 µg; PBMC) or native peripheral blood polymorphonuclear leukocytes (20 µg; PMN) resolved on a reducing 4-20% SDS-PAGE gel. Note the distinct presence of HECA-452-reactive ~100 kDa and ~65 kDa bands in G-CSF mobilized leukocytes. In all experiments, rat IgM isotype control blots performed in parallel lacked staining. Results presented are representative of observations on numerous HECA-452 blots from numerous clinical samples of G-CSF MPB. (C) Is a bar graph of CHO-E that were perfused over SDS-PAGE immunoblots of HECA-452 reactive membrane glycoproteins of ML-M at 0.6 dyne/cm$^2$ and the number of interacting cells/mm$^2$ was tabulated as a function of molecular weight. The background binding was subtracted and the results compiled into an adhesion histogram. Results presented are representative of multiple runs and multiple observations on numerous HECA-452 blots of membrane preparations of ML-M. (D) Membrane preparations of ML-M (20 µg) were resolved on a reducing 4-20% SDS-PAGE gel and immunoblotted with E-selectin-Ig (E-Ig) chimera in the presence of Ca$^{2+}$. The E-Ig chimera reactive glycoproteins at ~220 kDa, ~130 kDa, ~100 kDa, and ~65 kDa corresponded exactly with the proteins stained by HECA-452. Result shown is representative of multiple observations on numerous E-Ig blots of various clinical specimens of ML-M. (E) Shows the results of E-Ig used to immunoprecipitate E-selectin ligands from membrane preparations of ML-M, and the resolved immunoprecipitate was blotted with HECA-452. HECA-452 stained E-Ig immunoprecipitated material at ~220 kDa, ~130 kDa, ~100 kDa and ~65 kDa bands.
Figure 2B:
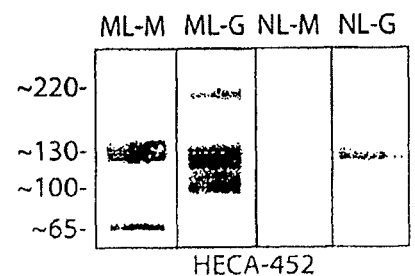
Figure 8:
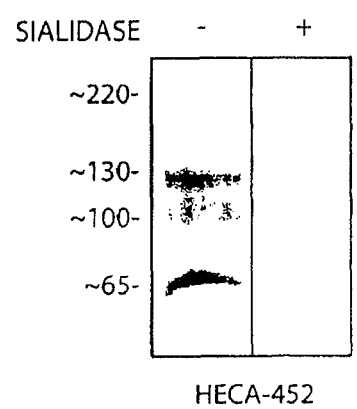
FIG. 8 shows HECA-452-reactive glycoproteins of ML are sensitive to sialidase treatment. Membrane preparations of ML-M (10 µg) were treated with sialidase (+) or buffer treated (−), resolved on a reducing 4-20% SDS-PAGE gel and immunoblotted with HECA-452. Absence of staining following sialidase digestion confirms specificity of HECA-452 staining for sialofucosylated carbohydrate modifications.

ML Express Hcell and a Novel HECA-452-Reactive ~65 kDa E-Selectin Glycoprotein Ligand To identify the E-selectin ligand(s) expressed by ML, we performed Western blot analysis using mAb HECA-452 as a probe. This mAb HECA-452 recognizes sialofucosylated oligosaccharides, prototypically sialyl lewis-X (sLe$^x$), that serve as selectin binding determinants and HECA-452 reactivity of glycoproteins correlates with E-selectin ligand activity[28,29]. Western-blot analysis of unfractionated ML lysates revealed several sialidase-sensitive HECA-452-reactive bands (~220 kDa, ~130 kDa, ~100 kDa, and ~65 kDa) (FIG. 2a and FIG. 8). Consistent with results of prior studies[30], unfractionated NL lysates revealed two prominent HECA-452-reactive bands (~220 kDa and ~130 kDa) (FIG. 2a). Notably, comparison of ML to NL showed no significant difference in HECA-452 staining of bands at ~220 kDa and ~130 kDa; however, ML lysates showed distinct and prominent HECA-452 staining at bands of ~100 kDa and ~65 kDa (FIG. 2a). Western blot analysis of membrane proteins of mononuclear (ML-M) and polymorphonuclear (ML-G) fractions of ML each showed the marked expression of HECA-452-reactive species of ~100 kDa and ~65 kDa (FIG. 2b).

Figure 2C:
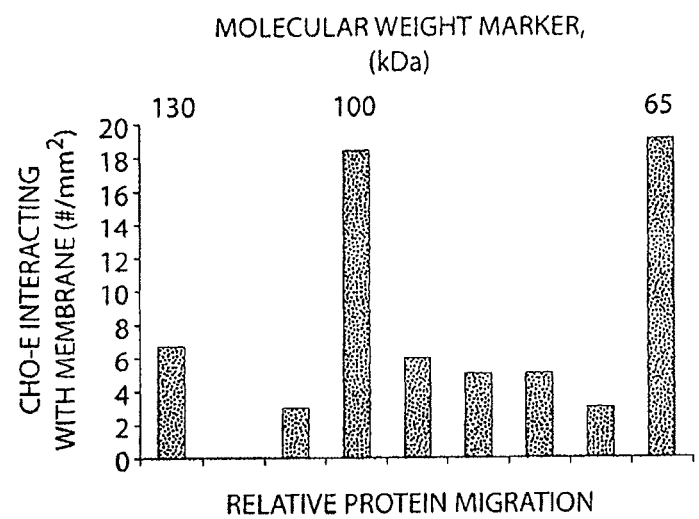

To determine whether the HECA-452-reactive membrane glycoproteins from ML represented E-selectin ligands, we utilized the blot-rolling assay[29,31]. For these experiments, we could not assess binding interactions over the entire lane due to the length restriction of the flow chamber; because the differences in HECA-reactivity in proteins from ML and NL clustered within mobilities encompassing 30 kDa-170 kDa, we set the field view over this range. Among ML lysates, E-selectin ligand activity was reproducibly observed on HECA-452 stained bands at ~130 kDa, ~100 kDa and ~65 kDa (FIG. 2c). Notably, the number of interacting CHO-E was much greater on the ~100 kDa and ~65 kDa bands compared to the ~130 kDa band (FIG. 2c), suggesting that these glycoproteins were major E-selectin ligands. Specificity for E-selectin binding was verified by significant diminution of CHO-E binding by addition of EDTA to cell suspension or by incubating cells with function blocking mAb to E-selectin (not shown). Moreover, no interactions were observed when mock-transfected CHO cells were perfused over HECA-452 blots of ML (not shown).

Figure 2D:
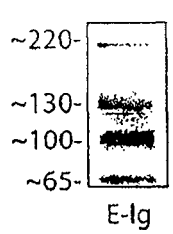
Figure 2E:
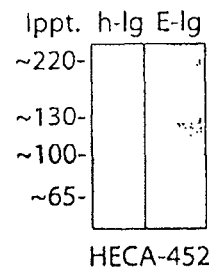
Figure 9A:
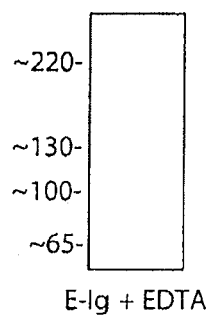
FIGS. 9A-B illustrate E-Ig-reactive glycoproteins of ML do not stain in the presence of EDTA or with control human-Ig. Membrane preparations of ML-M (20 µg) were resolved on a reducing 4-20% SDS-PAGE gel and immunoblotted with (A) E-selectin-Ig (E-Ig) chimera in the presence of 10 mM EDTA or (B) human-Ig. The E-Ig chimera reactive glycoproteins at ~220 kDa, ~130 kDa, ~100 kDa, and ~65 kDa (FIG. 2d) do not stain in the presence of EDTA or with control human-Ig. Results shown are typical of 2 separate experiments.
Figure 9B:
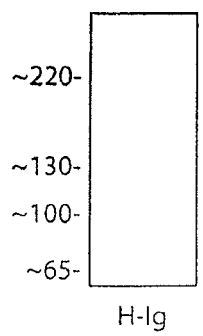

In a complementary approach, we probed the expression of E-selectin ligands using murine E-selectin-human Ig chimera (E-Ig) in ligand blots. E-Ig, in the presence of $Ca^{2+}$, stained ML-M membrane proteins at ~220 kDa, ~130 kDa, ~100 kDa, and ~65 kDa (FIG. 2d) corresponding with the HECA-452-reactive membrane glycoproteins, whereas these bands did not stain in the presence of EDTA or with control human-Ig (FIG. 9). HECA-452 blots of membrane proteins of ML-M immunoprecipitated using E-Ig also revealed staining at ~220 kDa, ~130 kDa, ~100 kDa and ~65 kDa (FIG. 2e). Control immunoprecipitates using human-Ig or E-Ig in the presence of EDTA showed absence of HECA-452-reactive proteins (FIG. 2e, and not shown). Collectively, these results show that the observed glycoproteins migrating at ~220 kDa, ~130 kDa, ~100 kDa and ~65 kDa represent the E-selectin ligands of ML.

Figure 3A:
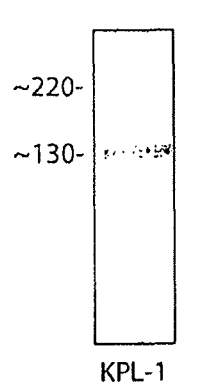
FIGS. 3A-F illustrates the characterization of PSGL-1, HCELL and a novel E-selectin ligand on ML. (A) Shows the membrane preparations of ML-M were resolved on a reducing 4-20% SDS PAGE gel, and immunoblotted with KPL-1, an antibody to PSGL-1. The bands at ~220 kDa and ~130 kDa corresponded with the HECA-452-reactive membrane glycoproteins on ML-M. Mouse $IgG_{1,k}$ isotype control blots performed in parallel lacked staining. (B) Shows that KPL-1 was used to immunoprecipitate PSGL-1, and the resolved immunoprecipitate was blotted with either HECA-452 or KPL-1. (C) Illustrates the membrane preparations of ML-M were resolved on a reducing 4-20% SDS PAGE gel, and immunoblotted with Hermes-1, an antibody to CD44. The band at ~100 kDa corresponded with the HECA-452-reactive membrane glycoprotein on ML-M. Rat IgG isotype control blots performed in parallel lacked staining. (D) Hermes-1 was used to immunoprecipitate CD44, and the resolved immunoprecipitate was blotted with either HECA-452 or another anti-human CD44 mAb, 2C5. (E) Is a graph showing the results of mAb Dreg-56 used to determine L-selectin expression on ML and NL using flow cytometry. $mIgG_{1,k}$ served as isotype control for Dreg-56. Results shown are typical of multiple clinical specimens. (F) Shows the results of L-selectin immunoprecipitated from biotinylated ML-M (MPB) and KG1a cells was resolved on a reducing SDS-PAGE gel, and immunoblotted with horseradish peroxidase (HRP) conjugated strepavidin. Note that the ~80 kDa L-selectin band is present in KG1a cells and absent in ML-M.
Figure 3B:
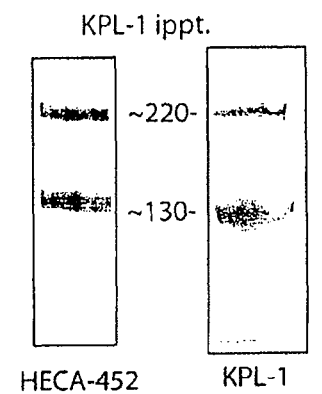
Figure 3C:
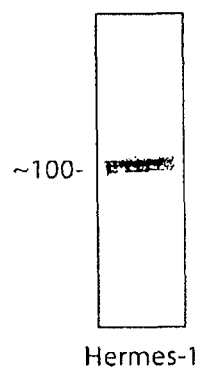
Figure 3D:
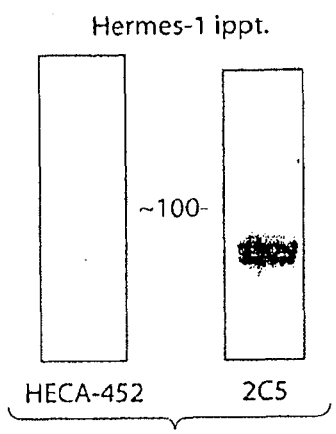

The electrophoretic mobilities of several bands bearing E-selectin ligand activity coincided with that of two previously characterized human E-selectin ligands, i.e., PSGL-1 (mw 220-240 kDa (dimer) and 120-140 kDa (monomer)) and the Hcell glycoform of CD44 (mw ~100 kDa)[28,31]. Thus, we sought to determine whether these bands represented these molecules. KPL-1 (anti-PSGL-1) blots of ML-M membrane proteins showed bands of ~220 kDa and ~130 kDa under reducing conditions (FIG. 3a). Subsequently, blots of immunoprecipitated PSGL-1 were stained with either HECA-452 or KPL-1. As shown in FIG. 3b, ML express both the monomer and dimer forms of PSGL-1, which represent the ~130 kDa and ~220 kDa HECA-452-reactive glycoproteins. Blots of ML-M membrane preparations stained with Hermes-1 (anti-CD44) showed a band of ~100 kDa under reducing conditions (FIG. 3c). Subsequently, blots of Hermes-1-immunoprecipitated CD44 were stained with either HECA-452 or 2C5, another anti-human CD44 antibody. As shown in FIG. 3d, ML express Hcell, evident as a HECA-452-reactive glycoform of CD44[28].

Figure 3F:
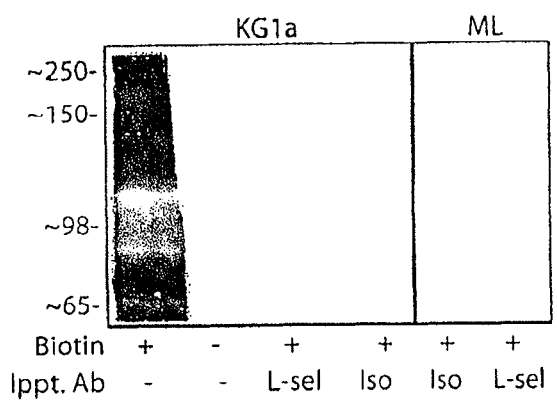
Figure 10:
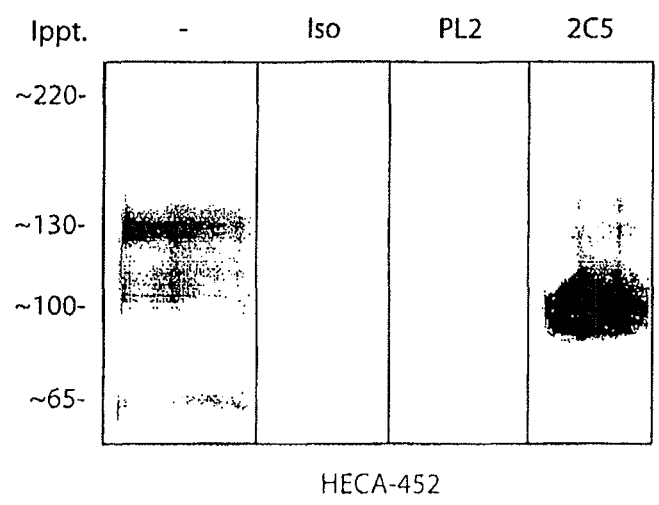
FIG. 10 shows HECA-452-reactive ~65 kDa E-selectin ligand does not appear to be related to PSGL-1 or CD44. PL2 and 2C5 were used to immunoprecipitate PSGL-1 and CD44, respectively, from membrane preparations of ML-M. Mouse $IgG_1$ was used as an isotype control for immunoprecipitation. The immunoprecipitated materials were resolved on a reducing 4-20% SDS PAGE gel, and immunoblotted with HECA-452. Note that PL-2 and 2C5 did not immunoprecipitate the HECA-452-reactive ~65 kDa glycoprotein.

The HECA-452-reactive ~65 kDa glycoprotein was not immunoprecipitated by mAbs KPL-1 or Hermes-1 (FIGS. 3b and 3d). Other mAbs to PSGL-1 (e.g., PL-2) and CD44 (e.g., 2C5) also did not immunoprecipitate the ~65 kDa protein (FIG. 10), suggesting that this protein is not related to either PSGL-1 or CD44. Human neutrophil L-selectin (mw ~75-90 kDa) has been reported to be an E-selectin ligand[32]. Since the HECA-452-reactive ~65 kDa glycoprotein resolved in Western blots in the molecular weight range of L-selectin[33], we investigated whether this structure was L-selectin. Flow cytometry revealed that ML express little L-selectin (FIG. 3e). This observation is consistent with a previous study demonstrating that G-CSF treatment of leukocytes down-regulates L-selectin expression[34]. In agreement with the flow cytometry results, we were unable to detect L-selectin in immunoprecipitates of ML-M (FIG. 3f). Collectively, these data demonstrate that PSGL-1 and Hcell serve as E-selectin ligands on ML and that the HECA-452-reactive ~65 kDa protein is not a glycoform of PSGL-1, CD44 or L-selectin.

Example 4

ML Possess Enhanced Levels of ST3GalIV, FucT-IV and FucT-VII

The capacity of E-selectin to recognize its relevant glycoprotein leukocyte ligand(s) is dependent on carbohydrate decoration of the core protein[18,28,35]. Based on prior observations that glycosyltransferases are regulated by cytokines[36], we sought to investigate whether G-CSF affects expression of relevant glycosyltransferases that create pertinent sialofucosylations. The carbohydrate modifications rendering the expression of E-selectin binding determinants are critically mediated by specific glycosyltransferases: α2,3-sialyltransferase (ST3GalIV) and leukocyte α1,3-fucosyltransferases (FucT-IV and FucT-VII)[37,38]. RT-PCR analysis of the expression of ST3GalIV, FucT-IV and FucT-VII revealed that the transcripts for each of these glycosyltransferases were increased in ML relative to NL (FIG. 4).

Example 5

Hcell and ~65 kDa Glycoprotein are Major E-Selectin Ligands on ML

Figure 5A:
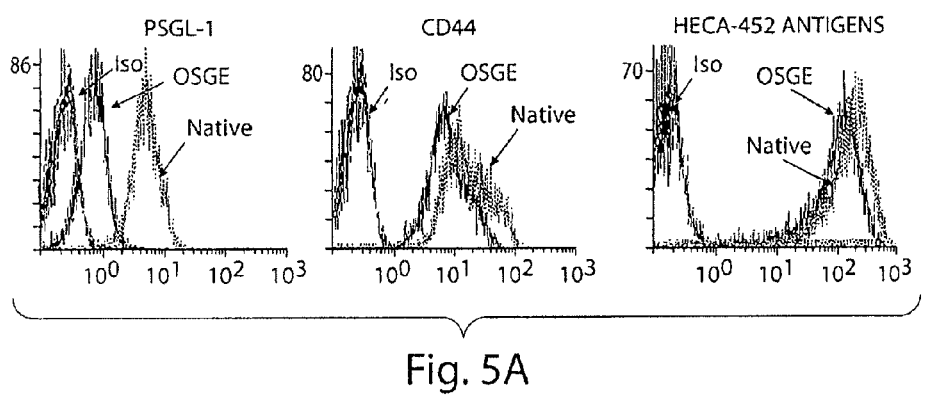
FIGS. 5A-C shows HCELL and ~65 kDa glycoprotein are major E-selectin ligands on ML. (A) Are graphs of PSGL-1, CD44 and HECA-452 antigen(s) expression determined on untreated (native) and OSGE-treated ML using flow cytometry. mAbs KPL-1 and F10-44-2 were used to determine expression of PSGL-1 and CD44, respectively. $mIgG_{1,k}$ and mIgM served as isotype controls for KPL-1 and F10-44-2, respectively. rIgM served as isotype control for HECA-452. Note that OSGE treatment abrogates surface expression of PSGL-1 and has minimal effect on expression of CD44 or HECA-452 antigen(s). Results shown are representative of 2 different experiments. (B) E-Ig blots of cell lysates from equal numbers of untreated (−) or 30 µg/ml OSGE treated (+) ML resolved on a reducing 4-20% SDS-PAGE gel. Note that OSGE treatment markedly abrogates E-selectin binding capacity of PSGL-1 with little to no effect on E-selectin binding capacity of HCELL and ~65 kDa E-selectin ligand. (C) Is a bar graph showing the results of HUVEC that were stimulated with TNF-α for 4-6 hrs. Subsequently, untreated (−) or OSGE (+) treated ML were perfused over HUVEC at 1.5 dyne/cm². Primary tethering of untreated or OSGE-treated ML on HUVEC was determined. Values are means±SE of n≥3 different runs.
Figure 5B:
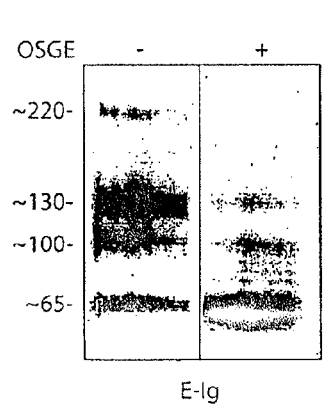
Figure 5C:
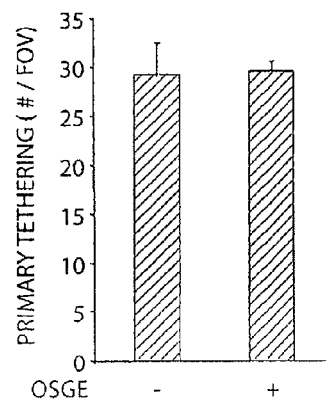
Figure 11A:
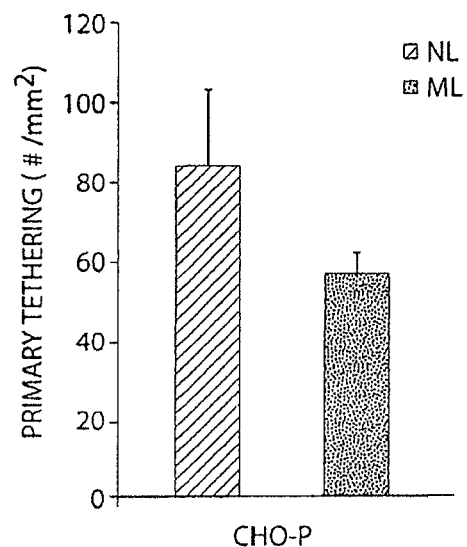
FIGS. 11A-B illustrates ML possess diminished binding to P-selectin relative to NL. ML or NL were perfused over CHO-P at 1.0 dyne/cm². (A) Illustrates primary tethering and (B) shows rolling velocity of ML or NL on CHO-P was determined. Values are means±SE of n≥6 different runs. * indicates statistically significant difference (p<0.05).
Figure 11B:
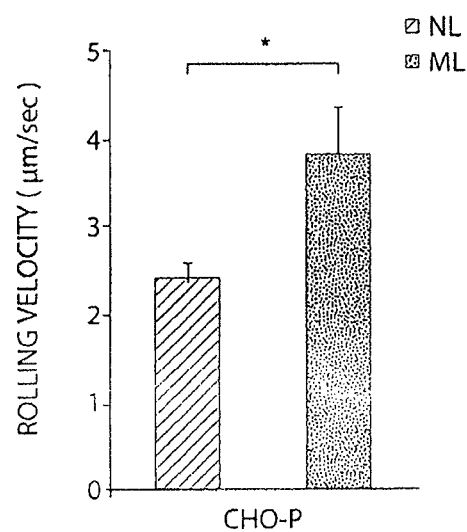

The E-/L-selectin ligand activity of Hcell is resistant to O-sialoglycoprotein endopeptidase (OSGE) treatment[28,31,39], whereas OSGE treatment abrogates PSGL-1 binding to all three selectins[40,41]. Accordingly, to determine the contribution of PSGL-1 to the observed enhanced E-selectin ligand activity of ML, we performed OSGE digestion and measured residual E-selectin binding activity. OSGE digestion of ML abrogated surface expression of PSGL-1 and had minimal effect on CD44 and HECA-452 antigen levels (FIG. 5a). E-Ig blots of cell lysates of ML showed distinct reduction of E-selectin binding by PSGL-1 on OSGE-treated cells (absent binding at dimer and marked diminution at monomer), while E-selectin binding determinants of Hcell and the ~65 kDa glycoprotein were intact (FIG. 5b). Despite significant decreases in PSGL-1 expression and function, OSGE treatment had no effect on primary tethering of ML on TNF-α-stimulated HUVEC (FIG. 5c). Combined, these data demonstrate that Hcell and the ~65 kDa glycoprotein are major E-selectin ligands on ML. Interestingly, compared to NL, ML displayed markedly diminished P-selectin-mediated and $Ca^{2+}$-dependent primary tethering on Chinese hamster ovary cells transfected with human P-selectin (CHO-P) (FIG. 11a). Furthermore, ML rolled significantly faster than NL on CHO-P (FIG. 11b). Given that PSGL-1 is the predominant ligand for P-selectin, the decreased PSGL-1 function on ML, combined with the findings that G-CSF treatment down-regulates PSGL-1 expression in humans[42], indicates that Hcell and ~65 kDa glycoprotein contribute to the augmented E-selectin binding of ML.

Example 6

Figure 6A:
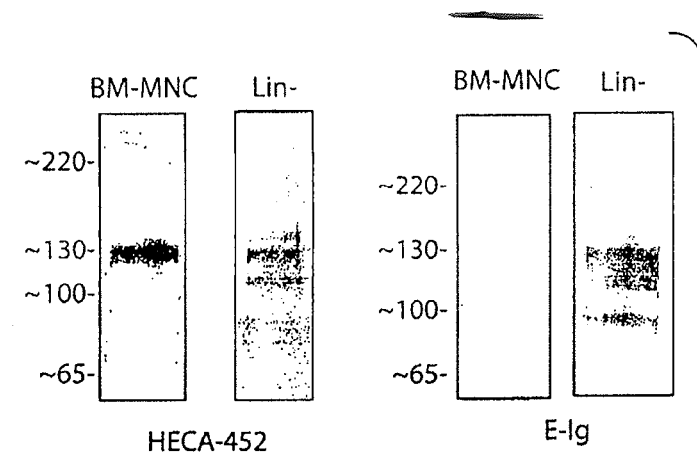
FIGS. 6A-E shows in vitro G-CSF treatment of human bone marrow (BM) cells up-regulates the expression of HCELL and HECA-452-reactive ~65 kDa glycoprotein. (A) (left) HECA-452 and (right) E-Ig blots of cell lysates from human BM mononuclear cells (BM-MNC) or BM CD34+/lineage-cells (Lin-) resolved on a reducing 4-20% SDS-PAGE gel. (B) (left) HECA-452 and (right) E-Ig blots of cell lysates from Band 1 (B1), Band 2 (B2) and Band 3 (B3) ML resolved on a reducing 4-20% SDS-PAGE gel. Note the presence of HCELL and HECA-452 reactive ~65 kDa glycoprotein predominantly in Band 1 and Band 2 cells. (C) (left) HECA-452 and (right) E-Ig blots of cell lysates from untreated (−) or 72 hr. G-CSF treated (+) Band 1, Band 2 and Band 3 human BM cells resolved on a reducing 4-20% SDS-PAGE gel. Note that G-CSF treatment results in a marked up-regulation of ~100 kDa HCELL and HECA-452-reactive ~65 kDa glycoprotein predominantly in immature myeloid cells. (D-E) Total RNA from equal numbers of untreated and G-CSF-treated Band 2 BM cells was subjected to RT-PCR followed by PCR amplification of pairs of cDNAs for ST3GalIV, FucT-IV, FucT-VII and the housekeeping gene GAPDH. (D) The net intensity of amplified bands was normalized to the net intensity of respective GAPDH controls. All values are means±SE of at least 3 different experiments. (E) Shows typical blots of PCR amplified products from untreated (U) and G-CSF-treated (G) Band 2 BM cells RNA are presented.
Figure 6B:
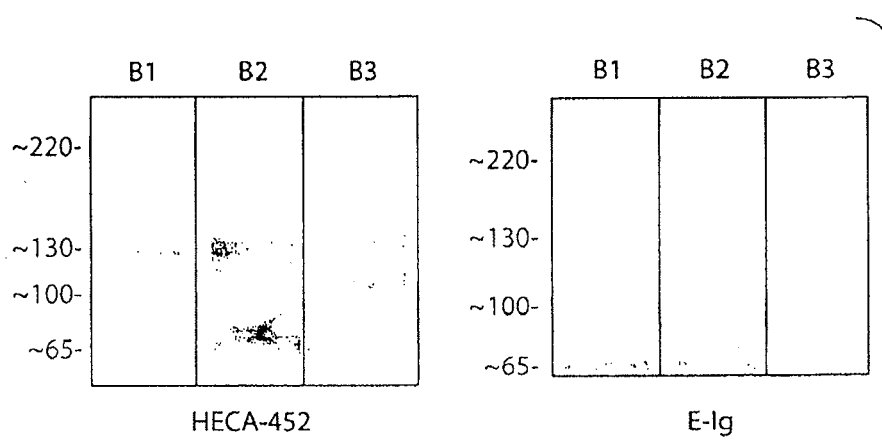
Figure 6C:
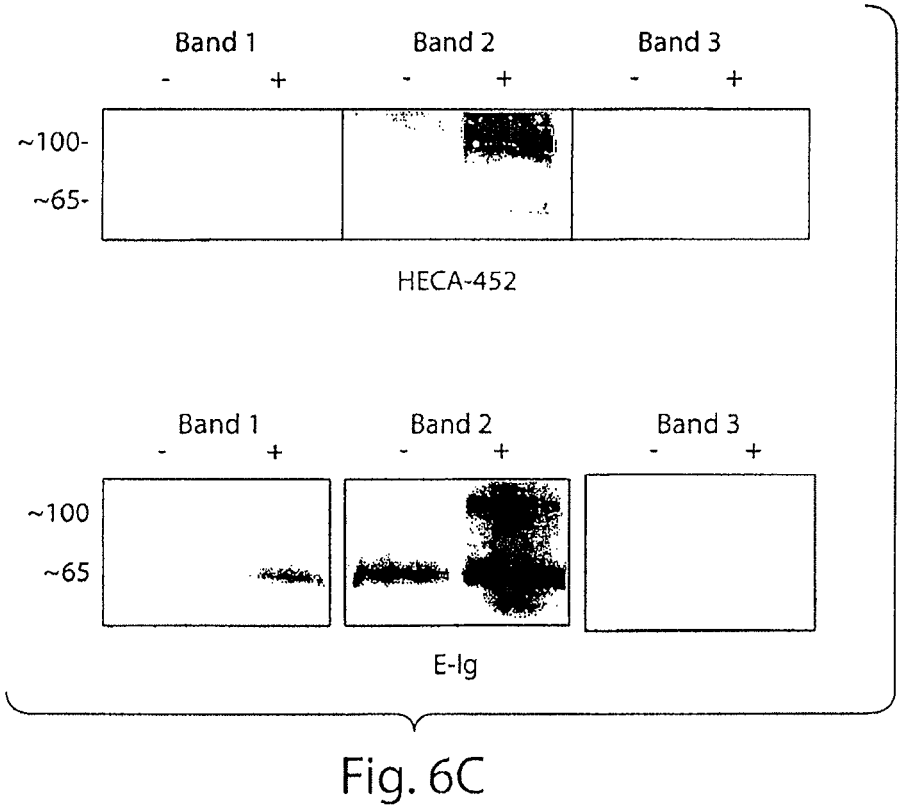
Figure 6D:
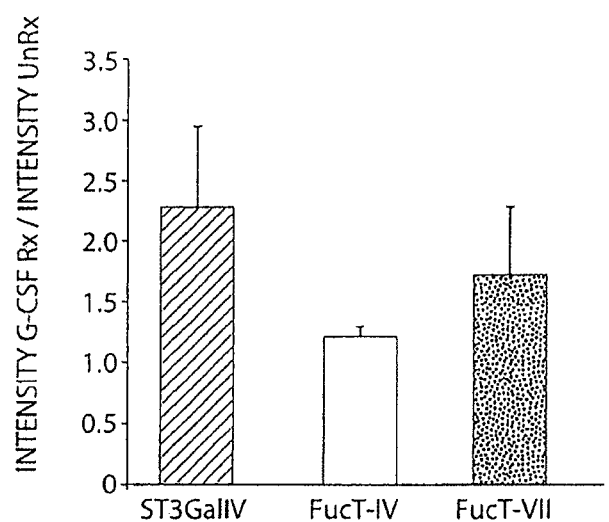
Figure 6E:
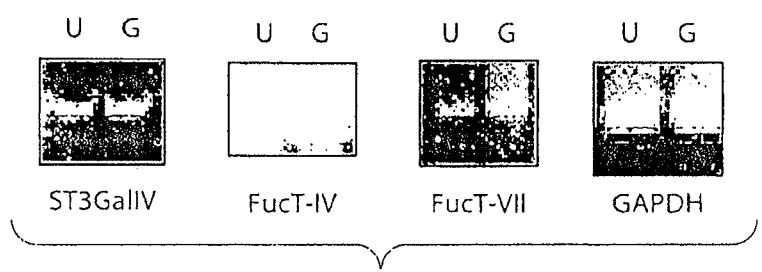
Figure 12A:
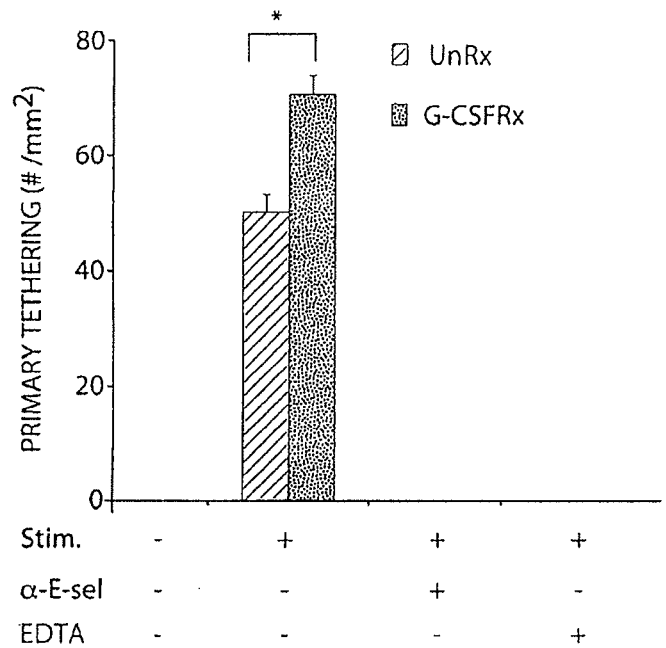
FIGS. 12A-B illustrates G-CSF treatment enhances the capability of human BM cells to adhere to endothelial E-selectin under physiologic flow conditions. HUVEC were stimulated with IL-1β for 4-6 hrs. Subsequently, untreated or 72 hr. G-CSF-treated Band 2 cells were perfused over HUVEC at 1.5 dyne/cm². In certain instances, stimulated HUVEC were pretreated with a mAb to E-selectin prior to use in adhesion assays. (A) Illustrates primary tethering and (B)
Figure 12B:
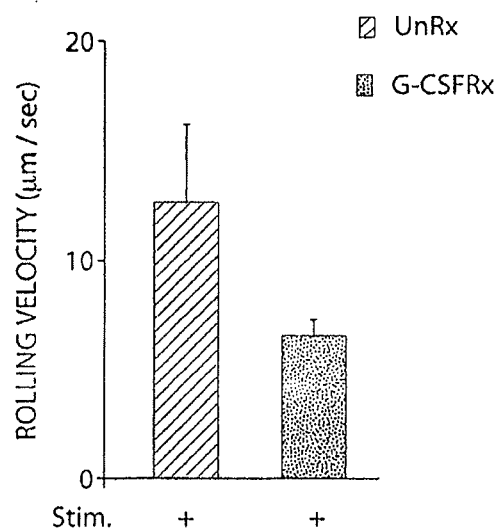

In vitro G-CSF Treatment of Human BM Cells Up-Regulates the Expression of ST3GalIV, FucT-IV and FucT-VII with Associated Increases in Expression of Hcell and HECA-452-Reactive ~65 kDa Glycoprotein and E-Selectin Binding While PSGL-1 is broadly expressed on myeloid, lymphoid and dendritic lineage cells[30,43] and also on CD34+ hematopoietic progenitor cells (FIG. 6a), Hcell is typically expressed only on CD34+ progenitors in human BM (FIG. 6a and[28]). Separation of ML into early immature (Band 1), late immature (Band 2) and mature (Band 3) myeloid fractions by Percoll gradient showed that predominantly Band 1 and Band 2 cells possessed Hcell and also expressed the HECA-452-reactive ~65 kDa glycoprotein (FIG. 6b). The presence of these structures in association with G-CSF administration prompted us to determine whether G-CSF directly induces their expression. Freshly isolated BM cells were separated into early immature (Band 1), late immature (Band 2) and mature (Band 3) myeloid fractions. The different subsets of cells were then cultured at 37° C. for 72 hr in the presence of 10 ng/ml G-CSF. Importantly, the in vitro dose of G-CSF utilized is well within the expected levels in human serum/extracellular fluids (after a single subcutaneous dose of 5 or 10 μg/kg, peak serum levels range from ~15.1 to ~100.5 ng/ml)[44,45]. The expression of Hcell and ~65 kDa glycoprotein were analyzed by reactivity to HECA-452 and E-Ig using Western blot analysis. In all experiments, efficacy of G-CSF treatment was confirmed by observing the down-regulation of L-selectin expression on G-CSF treated cells relative to untreated cells (not shown). As shown in FIG. 6c, G-CSF treatment consistently resulted in up-regulation in expression of Hcell and the HECA-452-reactive ~65 kDa glycoprotein predominantly on immature Band 1 and Band 2 cells. In association with G-CSF-induced increases in HCELL and HECA-452-reactive ~65 kDa protein, in vitro treatment of immature human BM cells (Band 2) with G-CSF resulted in increases in expression levels of ST3GalIV, FucT-IV and FucT-VII (FIGS. 6d and 6e) together with enhanced E-selectin binding (FIG. 12).

Example 7

In vitro G-CSF Treatment of Human BM Cells and Blood Cells Up-Regulates the Expression of Fucosyltransferase IX (FuT-IX) with Associated Increases in Expression of CD15

Freshly isolated bone marrow and peripheral blood were t cultured at 37° C. for 72 hr in the presence of 10 ng/ml G-CSF. Treatment increases Fuct-IX expression in normal progenitors and in mobilized peripheral blood. (FIG. 13) Fuct-IX has been found to regulate CD15 expression (which is the non-sialylated core of sLex) and is expressed on the surface of neutrophils. CD15 plays a role in innate immunity in priming dendritic cells. Moreover, FTIX fucosylates internal lactosamine units yielding the VIM-2 epitope. While, the VIM-2 is not sLex, but it consists of a terminal sialic acid with an "internal fucosylation" that can function as an E-selectin ligand Example 8

In vitro G-CSF Treatment of Human BM Cells and Leukocytes Cells Up-Regulates the Expression of Sialidase with Associated Increases in Expression of CD15

Freshly isolated BM cells were separated into early immature (Band 1), late immature (Band 2) and mature (Band 3) myeloid fractions. Early immature bone marrow cells, late mature bone marrow cells and leukocytes were then cultured at 37° C. for 72 hr in the presence of 10 ng/ml G-CSF. Treatment of bone marrow and leukocytes resulted in an increase expression of sialidase. Treatment of early immature none marrow did not has an effect on the expression of CD15. However treatment of the late mature bone marrow and leukocytes resulted in an increased expression of CD15. Furthermore, this increase of CD15 could be prevented by the inhibition of sialidase with 2-deoxy-2,3-dehydro-N-acetyl-neuraminic acid (DANA). These results indicate that CD15 expression was a direct result of the increase of sialidase expression resulting from G-CSF treatment.

REFERENCES

1. Elfenbein, G. J. & Sackstein, R. Primed marrow for autologous and allogeneic transplantation: a review comparing primed marrow to mobilized blood and steady-state marrow. Exp Hematol 32, 327-39 (2004).
2. Lindemann, A. & Rumberger, B. Vascular complications in patients treated with granulocyte colony-stimulating factor (G-CSF). Eur J Cancer 29A, 2338-9 (1993).
3. Hill, J. M. & Bartunek, J. The end of granulocyte colony-stimulating factor in acute myocardial infarction? Reaping the benefits beyond cytokine mobilization. Circulation 113, 1926-8 (2006).
4. Azoulay, E., Attalah, H., Harf, A., Schlemmer, B. & Delclaux, C. Granulocyte colony-stimulating factor or neutrophil-induced pulmonary toxicity: myth or reality? Systematic review of clinical case reports and experimental data. Chest 120, 1695-701 (2001).
5. Azoulay, E. et al. Exacerbation by granulocyte colony-stimulating factor of prior acute lung injury: implication of neutrophils. Crit Care Med 30, 2115-22 (2002).
6. Arimura, K. et al. Acute lung Injury in a healthy donor during mobilization of peripheral blood stem cells using granulocyte-colony stimulating factor alone. Haematologica 90, ECR10 (2005).
7. Fukumoto, Y. et al. Angina pectoris occurring during granulocyte colony-stimulating factor-combined preparatory regimen for autologous peripheral blood stem cell transplantation in a patient with acute myelogenous leukaemia. Br J Haematol 97, 666-8 (1997).
8. Mossner, R., Beckmann, I., Hallermann, C., Neumann, C. & Reich, K. Granulocyte colony-stimulating-factor-induced psoriasiform dermatitis resembles psoriasis with regard to abnormal cytokine expression and epidermal activation. Exp Dermatol 13, 340-6 (2004).
9. Dereure, O., Hillaire-Buys, D. & Guilhou, J. J. Neutrophil-dependent cutaneous side-effects of leucocyte colony-stimulating factors: manifestations of a neutrophil recovery syndrome? Br J Dermatol 150, 1228-30 (2004).
10. Jain, K. K. Cutaneous vasculitis associated with granulocyte colony-stimulating factor. J Am Acad Dermatol 31, 213-5 (1994).
11. Stricker, R. B. & Goldberg, B. G-CSF and exacerbation of rheumatoid arthritis. Am J Med 100, 665-6 (1996).
12. Adler, B. K. et al. Fatal sickle cell crisis after granulocyte colony-stimulating factor administration. Blood 97, 3313-4 (2001).
13. Hill, J. M. et al. Outcomes and risks of granulocyte colony-stimulating factor in patients with coronary artery disease. J Am Coll Cardiol 46, 1643-8 (2005).
14. Harada, M. et al. G-CSF prevents cardiac remodeling after myocardial infarction by activating the Jak-Stat pathway in cardiomyocytes. Nat Med 11, 305-11 (2005).
15. Butcher, E. C. Leukocyte-endothelial cell recognition: three (or more) steps to specificity and diversity. Cell 67, 1033-6 (1991).
16. Sackstein, R. The lymphocyte homing receptors: gatekeepers of the multistep paradigm. Curr Opin Hematol 12, 444-50 (2005).
17. van der Wal, A. C., Das, P. K., Tigges, A. J. & Becker, A. E. Adhesion molecules on the endothelium and mononuclear cells in human atherosclerotic lesions. Am J Pathol 141, 1427-33 (1992).
18. Kansas, G. S. Selectins and their ligands: current concepts and controversies. Blood 88, 3259-87 (1996).
19. Albert, R. K. Mechanisms of the adult respiratory distress syndrome: selectins. Thorax 50 Suppl 1, S49-52 (1995).
20. Kriegsmann, J. et al. Expression of E-selectin messenger RNA and protein in rheumatoid arthritis. Arthritis Rheum 38, 750-4 (1995).
21. Groves, R. W., Allen, M. H., Barker, J. N., Haskard, D. O. & MacDonald, D. M. Endothelial leucocyte adhesion molecule-1 (ELAM-1) expression in cutaneous inflammation. Br J Dermatol 124, 117-23 (1991).
22. Glass, L. F., Fotopoulos, T. & Messina, J. L. A generalized cutaneous reaction induced by granulocyte colony-stimulating factor. J Am Acad Dermatol 34, 455-9 (1996).
23. Bussolino, F. et al. Granulocyte- and granulocyte-macrophage-colony stimulating factors induce human endothelial cells to migrate and proliferate. Nature 337, 471-3 (1989).
24. Fuste, B. et al. Granulocyte colony-stimulating factor increases expression of adhesion receptors on endothelial cells through activation of p38 MAPK. Haematologica 89, 578-85 (2004).
25. Sipkins, D. A. et al. In vivo imaging of specialized bone marrow endothelial microdomains for tumour engraftment. Nature 435, 969-73 (2005).
26. Smith, M. L., Olson, T. S. & Ley, K. CXCR2- and E-selectin-induced neutrophil arrest during inflammation in vivo. J Exp Med 200, 935-9 (2004).
27. Kunkel, E. J. & Ley, K. Distinct phenotype of E-selectin-deficient mice. E-selectin is required for slow leukocyte rolling in vivo. Circ Res 79, 1196-204 (1996).
28. Dimitroff, C. J., Lee, J. Y., Rafii, S., Fuhlbrigge, R. C. & Sackstein, R. CD44 is a major E-selectin ligand on human hematopoietic progenitor cells. J Cell Biol 153, 1277-86 (2001).
29. Fuhlbrigge, R. C., King, S. L., Dimitroff, C. J., Kupper, T. S. & Sackstein, R. Direct real-time observation of E- and P-selectin-mediated rolling on cutaneous lymphocyte-associated antigen immobilized on Western blots. J Immunol 168, 5645-51 (2002).
30. Kieffer, J. D. et al. Neutrophils, monocytes, and dendritic cells express the same specialized form of PSGL-1 as do skin-homing memory T cells: cutaneous lymphocyte antigen. Biochem Biophys Res Commun 285, 577-87 (2001).
31. Dimitroff, C. J., Lee, J. Y., Fuhlbrigge, R. C. & Sackstein, R. A distinct glycoform of CD44 is an L-selectin ligand on human hematopoietic cells. Proc Natl Acad Sci U S A 97, 13841-6 (2000).
32. Zollner, O. et al. L-selectin from human, but not from mouse neutrophils binds directly to E-selectin. J Cell Biol 136, 707-16 (1997).
33. Schleiffenbaum, B., Spertini, O. & Tedder, T. F. Soluble L-selectin is present in human plasma at high levels and retains functional activity. J Cell Biol 119, 229-38 (1992).
34. Ohsaka, A. et al. Granulocyte colony-stimulating factor down-regulates the surface expression of the human leucocyte adhesion molecule-1 on human neutrophils in vitro and in vivo. Br J Haematol 84, 574-80 (1993).
35. Fuhlbrigge, R. C., Kieffer, J. D., Armerding, D. & Kupper, T. S. Cutaneous lymphocyte antigen is a specialized form of PSGL-1 expressed on skin-homing T cells. Nature 389, 978-81 (1997).
36. Wagers, A. J., Waters, C. M., Stoolman, L. M. & Kansas, G. S. Interleukin 12 and interleukin 4 control T cell adhesion to endothelial selectins through opposite effects on alpha1, 3-fucosyltransferase VII gene expression. J Exp Med 188, 2225-31 (1998).
37. Ellies, L. G. et al. Sialyltransferase specificity in selectin ligand formation. Blood 100, 3618-25 (2002).
38. Wagers, A. J., Stoolman, L. M., Kannagi, R., Craig, R. & Kansas, G. S. Expression of leukocyte fucosyltransferases regulates binding to E-selectin: relationship to previously implicated carbohydrate epitopes. J Immunol 159, 1917-29 (1997).
39. Dimitroff, C. J., Lee, J. Y., Schor, K. S., Sandmaier, B. M. & Sackstein, R. Differential L-selectin binding activities of human hematopoietic cell L-selectin ligands, Hcell and PSGL-1. J Biol Chem 276, 47623-31 (2001).
40. Goetz, D. J. et al. Isolated P-selectin glycoprotein ligand-1 dynamic adhesion to P- and E-selectin. J Cell Biol 137, 509-19 (1997).
41. Spertini, O., Cordey, A. S., Monai, N., Giuffre, L. & Schapira, M. P-selectin glycoprotein ligand 1 is a ligand for L-selectin on neutrophils, monocytes, and CD34+ hematopoietic progenitor cells. J Cell Biol 135, 523-31 (1996).
42. Jilma, B. et al. Rapid down modulation of P-selectin glycoprotein ligand-1 (PSGL-1, CD162) by G-CSF in humans. Transfusion 42, 328-33 (2002).
43. Laszik, Z. et al. P-selectin glycoprotein ligand-1 is broadly expressed in cells of myeloid, lymphoid, and dendritic lineage and in some nonhematopoietic cells. Blood 88, 3010-21 (1996).
44. van Der Auwera, P. et al. Pharmacodynamics and pharmacokinetics of single doses of subcutaneous pegylated human G-CSF mutant (Ro 25-8315) in healthy volunteers: comparison with single and multiple daily doses of filgrastim. Am J Hematol 66, 245-51 (2001).
45. Faulkner, L. B. et al. G-CSF serum pharmacokinetics during peripheral blood progenitor cell mobilization: neutrophil count-adjusted dosage might potentially improve mobilization and be more cost-effective. Bone Marrow Transplant 21, 1091-5 (1998).
46. Hakansson, L. et al. Effects of in vivo administration of G-CSF on neutrophil and eosinophil adhesion. Br J Haematol 98, 603-11 (1997).
47. Xia, L. et al. P-selectin glycoprotein ligand-1-deficient mice have impaired leukocyte tethering to E-selectin under flow. J Clin Invest 109, 939-50 (2002).
48. Yang, J. et al. Targeted gene disruption demonstrates that P-selectin glycoprotein ligand 1 (PSGL-1) is required for P-selectin-mediated but not E-selectin-mediated neutrophil rolling and migration. J Exp Med 190, 1769-82 (1999).
49. Zou, X. et al. PSGL-1 Derived from Human Neutrophils is a High Efficiency Ligand for Endothelial Expressed E-selectin under Flow. Am J Physiol Cell Physiol (2005).
50. Cowland, J. B. & Borregaard, N. Isolation of neutrophil precursors from bone marrow for biochemical and transcriptional analysis. J Immunol Methods 232, 191-200 (1999).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for increasing cell surface expression or activity of an E-selectin ligand on a human myeloid cell comprising contacting the myeloid cell with granulocyte colony stimulating factor (G-CSF) and a sialidase inhibitor, thereby increasing cell surface expression or activity of an E-selectin ligand on the cell.

2. The method of claim 1, wherein a plurality of human myeloid cells are provided.

3. The method of claim 1, wherein the myeloid cell is allogeneic.

4. The method of claim 1, wherein the myeloid cell is provided ex vivo.

5. The method of claim 1, wherein the myeloid cell is contacted with G-CSF in vitro.

6. The method of claim 1, wherein the E-selectin ligand Is a hematopotetic cell E-selectin ligand (HCELL) polypeptide.

7. The method of claim 1, wherein said method increases the expression of a HECA-452-reactive epitope on the cell.

8. The method of claim 7, wherein the cell is administered to a subject as part of treatment with hematopoietic stem cell transplantation.

9. The method of claim 7, wherein the cell is administered to a subject who is in need of treatment for tissue injury.

10. The method of claim 7, wherein the cell is a native human myeloid cell.

11. The method of claim 7, wherein the cell is a native human immature myeloid cell.

12. The method of claim 1, wherein the cell is contacted with the G-CSF and sialidase inhibitor ex vivo, and wherein the method further comprises administering the cell to a subject in need thereof.

13. The method of claim 12, wherein the myeloid cell is autologous.

14. The method of claim 1, wherein the sialidase inhibitor is 2-deoxy-2,3-dehydro-N-acetyl-neuraminic acid (DANA).

15. The method of claim 1, wherein the cell is administered to a subject as part of treatment with hematopoietic stem cell transplantation.

16. The method of claim 1, wherein the cell is administered to a subject as part of treatment for infection.

17. The method of claim 1, wherein the cell is administered to a subject who is in need of treatment for tissue injury.

18. The method of claim 1, wherein the cell is a native human myeloid cell.

19. The method of claim 1, wherein the cell is a native human immature myeloid cell.

20. The method of claim 1, wherein the cell is a myeloid cell and wherein the method increases the ability of the cell to migrate to endothelial beds expressing E-selectin.

* * * * *